(12) United States Patent
Chen et al.

(10) Patent No.: US 12,042,484 B2
(45) Date of Patent: *Jul. 23, 2024

(54) TIZANIDINE LIQUID PREPARATION AND USE THEREOF

(71) Applicant: FIDELITY BIOPHARMA CO., New Haven, CT (US)

(72) Inventors: Gang Chen, Sichuan (CN); Gongzheng Chen, Sichuan (CN); Song Lin, Sichuan (CN); Rashmi Rohit Prasade, Sichuan (CN); Ganesh Dattatray Chavan Patil, Sichuan (CN)

(73) Assignee: FIDELITY BIOPHARMA CO., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/395,225

(22) Filed: Dec. 22, 2023

(65) Prior Publication Data

US 2024/0148703 A1    May 9, 2024

Related U.S. Application Data

(63) Continuation-in-part of application No. 17/918,130, filed as application No. PCT/CN2022/091371 on May 7, 2022.

(30) Foreign Application Priority Data

May 26, 2021 (CN) .......................... 202110577512.4

(51) Int. Cl.
| | | |
|---|---|---|
| *A61K 31/433* | (2006.01) | |
| *A61K 9/00* | (2006.01) | |
| *A61K 9/08* | (2006.01) | |
| *A61K 47/02* | (2006.01) | |
| *A61K 47/10* | (2017.01) | |
| *A61K 47/12* | (2006.01) | |
| *A61K 47/14* | (2017.01) | |
| *A61K 47/18* | (2017.01) | |
| *A61K 47/26* | (2006.01) | |
| *A61K 47/38* | (2006.01) | |

(52) U.S. Cl.
CPC .......... *A61K 31/433* (2013.01); *A61K 9/0053* (2013.01); *A61K 9/08* (2013.01); *A61K 47/02* (2013.01); *A61K 47/10* (2013.01); *A61K 47/12* (2013.01); *A61K 47/14* (2013.01); *A61K 47/183* (2013.01); *A61K 47/26* (2013.01); *A61K 47/38* (2013.01)

(58) Field of Classification Search
CPC .................................................... A61K 31/433
See application file for complete search history.

(56) References Cited

U.S. PATENT DOCUMENTS

| | | | | |
|---|---|---|---|---|
| 8,883,830 | B2 * | 11/2014 | Aung-Din ............ | A61K 31/551 514/288 |
| 2020/0121675 | A1 | 4/2020 | Whitcup et al. | |

FOREIGN PATENT DOCUMENTS

| | | |
|---|---|---|
| CN | 105566314 A | 5/2016 |
| CN | 110563715 A | 12/2019 |
| CN | 110582294 A | 12/2019 |
| EP | 2338473 A1 | 6/2011 |
| IN | 201921012764 A | 2/2020 |

OTHER PUBLICATIONS

PCT/CN2022/091371 International Search Report and Written Opinion dated Aug. 10, 2022, 6 pages.
Gobetti, C. et al. "Development and Stability Control of Pediatric Oral Tizanidine Hydrochloride Formulations for Hospital Use", AAPS PharmSciTech, vol. 21, No. 6, Jul. 2020, 11 pages.
Chinese Patent Application No. 202110577512.4, First Office Action with English translation dated Dec. 16, 2023, 13 pages.

* cited by examiner

*Primary Examiner* — Rei Tsang Shiao
(74) *Attorney, Agent, or Firm* — COZEN O'CONNOR

(57) ABSTRACT

A tizanidine liquid preparation and use of the tizanidine liquid preparation in the preparation of a medicament for treating muscle spasm, wherein the tizanidine liquid preparation comprises an active ingredient, disodium EDTA and other pharmaceutical excipients, wherein the active ingredient is one or more of tizanidine or a pharmaceutically acceptable salt, solvate and hydrate thereof.

29 Claims, No Drawings

TIZANIDINE LIQUID PREPARATION AND USE THEREOF

This application is a Continuation-in-part (CIP) of U.S. patent application Ser. No. 17/918,130 filed Oct. 11, 2022, which is a US national stage application of PCT application PCT/CN2022/091371 filed May 7, 2022, which claims the priority of Chinese Patent Application No. 202110577512.4, filed with the China National Intellectual Property Administration on May 26, 2021. The entire contents of all of the above-mentioned applications are hereby incorporated by reference into this disclosure.

FIELD

The present disclosure relates to the field of medicine, and in particular to a tizanidine liquid preparation and use thereof.

BACKGROUND

Tizanidine is a central α-2 adrenergic agonist used to treat muscle spasm.

The chemical structure of tizanidine is shown as follows:

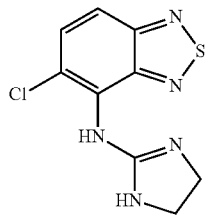 [SMILES: Clc1ccc2nsnc2c1NC1=NCCN1]

Tizanidine is currently marketed under the trademark Zanaflex® for the treatment of muscle spasm caused by spinal cord injury or multiple sclerosis.

The elderly population accounts for the largest proportion of tizanidine formula drug users. According to the Medical Expenditure Panel Survey (MEPS) of American Agency for Healthcare Research and Quality (AHRQ), about 2.06 million people are prescribed tizanidine. According to prescription drug use data from MEDICARED in the United States, about 1.46 million elderly/disabled/severely ill patients were prescribed tizanidine in 2018. It can be estimated that the elderly accounted for more than 60%.

Elderly people with neurological diseases are more likely to suffer from dysphagia: dysphagia is a common clinical symptom, and central nervous system diseases are common diseases that cause dysphagia. In foreign countries, the incidence of dysphagia in acute stroke patients is 37%-78%; in China, the incidence of dysphagia in acute stroke patients is 51%-73%. Although most patients recovered swallowing function 1 month after stroke, some patients still have dysphagia 6 months after stroke. The overall prevalence of dysphagia in MS patients is about 33-43%, the incidence of dysphagia with acute cervical spinal cord injury is about 30.9%, and the incidence of dysphagia with brain injury is 27-30%.

Solid oral dosage forms play the largest and most important role in the overall pharmaceutical preparation. At present, most of the tizanidine dosage forms on the market are ordinary tablets, and there are also capsule preparations. Because drinking water is generally needed to help swallowing when taking the drugs in ordinary tablets/capsule preparations, tizanidine hydrochloride ordinary tablets/capsule preparations have poor compliance for some special groups such as young children, the elderly, patients with dysphagia, patients with certain mental illnesses, and patients who have difficulty in changing their position in bed, which cannot meet the needs of clinical medication. In clinical practice, tablets are often crushed or capsules are often opened and then administered to patients with dysphagia. Crushing/opening/mixing with other drugs for administration may cause risks of adverse effects and medical errors. Since large number of patients have difficulty in swallowing solid oral dosage forms, various solid forms of oral drugs such as buccal tablets, sublingual tablets, effervescent tablets, chewable tablets, orally disintegrating tablets, and soluble tablets have been developed in medicine.

There are certain limitations in the dose titration process of oral solid preparations: 1) the dose division is inaccurate; 2) multiple specifications need to be developed, and the cost of preparation development for enterprises becomes high; 3) during the dose titration process according to the change of patient's condition, the changes of specifications required can easily lead to waste. However, liquid preparations do not have the above problems during the dose titration process.

It can be seen that, compared with oral solid preparations, the development of tizanidine liquid preparations has the advantage of more convenient adjustment of dose titration, and it is also easy to improve compliance of taking medicine for those such as young children, the elderly, patients with dysphagia, patients with certain mental illnesses, and patients who have difficulty in changing their position in bed, thereby meeting the clinical needs.

It is well known that liquid active pharmaceutical preparations are more susceptible to chemical instability than solid active pharmaceutical preparations. Although liquid active pharmaceutical preparations have obvious clinical advantages, preparation developers are often discouraged due to their stability problem.

The impurity detection of related substances in the drug is an important indicator to measure the chemical stability of drugs. The higher the impurity content of the related substances is, the worse the chemical stability is. The chemical stability of liquid preparations greatly affects its clinical promotion and use, and the impurity content of the related substances affects the safety of medication, wherein the more impurities are, the greater the possible medication risk is.

Since there is no marketed product of tizanidine liquid preparations on the market at present, the Pharmacopoeia has not made relevant specifications on the related substances of tizanidine liquid preparations. Therefore, for related substances of tizanidine liquid preparations, one should reference the relevant regulations on the related substances of tizanidine tablets in the Chinese Pharmacopoeia—the total impurity amount of the related substances in tizanidine tablets shall not exceed 0.5%.

At present, the ordinary tablets and capsule preparations of tizanidine on the market have a high probability of adverse effects after being administered to human body. Taking Zanaflex® (tizanidine hydrochloride) tablets and capsules as an example, it is stated in their instructions that under single-dose administration, among the adverse effects in patients, the incidence of 'somnolence' alone is as high as 78% (single dose of 8 mg)/92% (single dose of 16 mg). Adverse effect of drug refers to the reaction generated during the use of drug with normal usage and dosage, which is irrelevant to the purpose of the drug use or harmful to the body, not only referring to the side effect of the drug. The quality, dosage form, impurities, excipients, content and the like of drugs are all factors that cause drug adverse effects. The adverse effects of tizanidine ordinary tablets and capsule preparations greatly affect the safety of tizanidine drug use. Meanwhile, the high incidence of somnolence (i.e., drowsiness) among its adverse effects also affects the normal life of the patients taking the medicine to a certain extent, and greatly reduces the compliance of patients taking the medicine. Therefore, how to reduce the incidence of adverse effects in normal use of tizanidine drugs is of great significance to enhance the safety of drug use and the compliance of patients taking the medicine.

Moreover, for muscle spasm, the faster the drug acts, the more quickly the pain of patients can be relieved. For oral drugs, food often has a great impact on the speed of drug action, and the drug peak time of the existing tizanidine ordinary tablets and capsule preparations under a postprandial condition is significantly prolonged, which is not conducive to quickly reducing the pain of patients. Therefore, how to reduce the impact of food on the peak time of the drug and speed up the drug action of tizanidine under a post-prandial condition is also one of the problems to be solved.

In addition to consideration of the factors such as stability, adverse effects and drug action speed in the development of new liquid drug dosage form of tizanidine, the influence of changes of dosage form on drug efficacy is also a factor that must be considered. The dosage form of the drug determines the route and method of administration, which directly affects the degree of drug absorption, thereby affecting the drug efficacy. The physical and chemical properties of the drug will directly affect the release of the drug, thereby affecting the therapeutic effect of the drug. The selection of excipients in the drug preparation not only affects the production process and the appearance and physical properties of the preparation, but also will change the bioavailability of the preparation, thereby affecting the efficacy of the preparation.

The present disclosure addresses issues in the field by providing a tizanidine liquid preparation with low content of impurities, strong stability, low adverse effects, and equivalent bioavailability to solid preparations. In one aspect, the rate of drug action of the disclosed composition is not affected much by whether a subject is fasting or fed. In another aspect, the disclosed liquid composition acts faster as compared to the solid composition under a post-prandial condition.

SUMMARY

One of the objectives of the present disclosure is to provide a tizanidine liquid preparation, which has low content of impurity and strong stability; compared to tizanidine solid preparations, it has low adverse effects, little effect of food on the drug action speed, fast drug action speed under a post-prandial condition, and equivalent bioavailability to solid preparations.

In one embodiment, the tizanidine liquid preparation comprises an active ingredient, disodium EDTA and other pharmaceutical excipients; wherein the active ingredient is one or more of tizanidine or a pharmaceutically acceptable salt, solvate and hydrate thereof.

Preferably, the pH value of the tizanidine liquid preparation is greater than 3.5 and smaller than 6.5.

Preferably, the pH value of the tizanidine liquid preparation is between 4.0 and 6.1.

Preferably, the tizanidine liquid preparation comprises solvent, and the solvent is water.

Preferably, the other pharmaceutical excipient is one or more of a pH adjusting agent, a preservative, a co-solvent, a thickening agent, a flavoring agent, a sweetening agent and a coloring agent.

Preferably, the pH adjusting agent is one or more of citric acid, ascorbic acid, acetic acid, tartaric acid, trisodium citrate, sodium citrate, potassium citrate, sodium phosphate, tricalcium phosphate, calcium carbonate, sodium bicarbonate, calcium phosphate, calcium carbonate, magnesium hydroxide, hydrochloric acid and sodium hydroxide;

In some embodiments, the co-solvent is one or more of sorbitol, maltitol, mannitol, isomaltose, xylitol, glucose and fructose;

In some embodiments, the preservative is one or more of sodium benzoate, ethylparaben, propylparaben, sodium methylparaben, sodium ethylparaben, sodium propylparaben, benzoic acid, potassium phenylpropionate, sorbic acid, sodium sorbate, calcium sorbate, potassium sorbate, dehydroacetic acid, sodium diacetate, and calcium propionate;

In some embodiments, the thickening agent is one or more of hypromellose, hydroxypropyl cellulose, colloidal silicon dioxide, methyl cellulose, sodium carboxymethyl cellulose, sodium alginate, and cyclodextrin;

In some embodiments, the flavoring agent is one- or more of strawberry flavoring agent, orange flavoring agent, banana flavoring agent, cherry flavoring agent, lemon flavoring agent, cardamom flavoring agent, fennel flavoring agent, mint flavoring agent, menthol flavoring agent and vanillin flavoring agent;

In some embodiments, the sweetening agent is one or more of sucralose, glycerin, sodium saccharin, glucose, stevia, stevioside, aspartame, sodium cyclamate, acesulfame potassium, alitame, and neotame;

In some embodiments, the coloring agent is one or more of amaranth red, carmine, erythrosine, new red, lemon yellow, sunset yellow, indigo, beet red, shellac red, bilberry red, capsicum red, and red rice red.

In some embodiments, the pH adjusting agent is a mixture of citric acid and sodium citrate;

In some embodiments, the preservative is a mixture of sodium methylparaben and sodium propylparaben, or sodium benzoate;

In some embodiments, the co-solvent is sorbitol;

In some embodiments, the thickening agent is a mixture of hydroxypropyl cellulose and colloidal silicon dioxide, or hydroxypropyl cellulose;

In some embodiments, the flavoring agent is strawberry flavoring agent;

In some embodiments, the sweetening agent is sucralose.

In some embodiments, each 100 mL of the liquid preparation comprises the following components:

0.02-1 g of active ingredient, 0-0.2 g of disodium EDTA; wherein the content of disodium EDTA is not 0.

Preferably, each 100 mL liquid preparation comprises the following components:

| Tizanidine | 0.02-1 g |
|---|---|
| Disodium EDTA | 0.005-0.2 g. |

Preferably, each 100 mL liquid preparation comprises the following components:

| | |
|---|---|
| Tizanidine | 0.02-1 g |
| Disodium EDTA | 0.005-0.2 g |
| Citric acid | 0.01-0.2 g |
| Sodium citrate | 0.01-0.1 g. |

Preferably, each 100 mL liquid preparation comprises the following components:

| | |
|---|---|
| Tizanidine | 0.04-0.09 g |
| Disodium EDTA | 0.008-0.12 g |
| Citric acid | 0.06-0.14 g |
| Sodium citrate | 0.02-0.06 g. |

In some embodiments, the tizanidine liquid preparation comprises the following components:
Tizanidine, sodium methylparaben, sodium propylparaben, disodium EDTA, sucralose, citric acid, sodium citrate, strawberry flavoring agent and water; or
tizanidine, sodium methylparaben, sodium propylparaben, sorbitol, disodium EDTA, sucralose, citric acid, sodium citrate, strawberry flavoring agent and water; or
tizanidine, hydroxypropyl cellulose, sodium methylparaben, sodium propylparaben, sorbitol, disodium EDTA, sucralose, citric acid, sodium citrate, strawberry flavoring agent and water; or
tizanidine, hydroxypropyl cellulose, colloidal silicon dioxide, sodium methylparaben, sodium propylparaben, sorbitol, disodium EDTA, sucralose, citric acid, sodium citrate, strawberry flavoring agent and water; or
tizanidine, hydroxypropyl cellulose, sodium benzoate, glycerin, sorbitol, disodium EDTA, sucralose, strawberry flavoring agent and water.

In some embodiments, each 100 mL liquid preparation comprises the following components:
Tizanidine hydrochloride 0.046 g, sodium methylparaben, 0.1 g, sodium propylparaben 0.01 g, disodium EDTA 0.1 g, sucralose 0.05 g, citric acid 0.083 g, sodium citrate 0.042 g, strawberry flavoring agent 0.05 g, and the remainder water; or
tizanidine hydrochloride 0.046 g, sodium methylparaben 0.1 g, sodium propylparaben 0.01 g, 70% sorbitol solution 25 g, disodium EDTA 0.1 g, sucralose 0.05 g, citric acid 0.09 g, sodium citrate 0.035 g, strawberry flavoring agent 0.05 g, and the remainder water; or
tizanidine hydrochloride 0.046 g, hydroxypropyl cellulose 2.5 g, sodium methylparaben 0.1 g, sodium propylparaben 0.01 g, 70% sorbitol solution 15 g, disodium EDTA 0.1 g, sucralose 0.05 g, citric acid 0.09 g, sodium citrate 0.046 g, strawberry flavoring agent 0.05 g, and the remainder water; or
tizanidine hydrochloride 0.046 g, hydroxypropyl cellulose 2.5 g, colloidal silicon dioxide 0.5 g, sodium methylparaben 0.1 g, sodium propylparaben 0.01 g, 70% sorbitol solution 15 g, disodium EDTA 0.1 g, sucralose 0.05 g, citric acid 0.09 g, sodium citrate 0.04 g, strawberry flavoring agent 0.05 g, and the remainder water; or
tizanidine hydrochloride 0.046 g, hydroxypropyl cellulose 5 g, sodium benzoate 0.1 g, glycerin 15 g, 70% sorbitol solution 25 g, disodium EDTA 0.1 g, sucralose 0.05 g, strawberry flavoring agent 0.05 g, and the remainder water.

In some embodiments, the active pharmaceutical ingredient in the tizanidine liquid preparation of the present disclosure is preferably tizanidine hydrochloride, in which the content of the active pharmaceutical ingredient tizanidine hydrochloride is 0.046 g/100 mL. In one aspect, the liquid preparation of the present disclosure also comprises disodium EDTA. In another aspect, when the liquid preparation is stored at room temperature, the total impurity amount of its related substances is ≤0.5%, or ≤0.2%, or ≤0.1%, or ≤0.05%. In another aspect, after the liquid preparation is administered to a subject, the mean value of $C_{max}$, mean value of $AUC_{0-t}$ and/or mean value of $AUC_{0-\infty}$ of tizanidine thereof are respectively within the range of 80%-125% of the mean value of $C_{max}$, mean value of $AUC_{0-t}$ and/or mean value of $AUC_{0-\infty}$ of the tizanidine in a solid dosage form (i.e., tablet or capsule) after being administered to the same or similar subject in equivalent doses with respect to tizanidine: In another aspect, after the liquid preparation is administered to a subject, the mean value of $C_{max}$, mean value of $AUC_{0-t}$ and/or mean value of $AUC_{0-\infty}$ of tizanidine thereof are respectively within the range of 80%-125% of the mean value of $C_{max}$, mean value of $AUC_{0-t}$ and/or mean value of $AUC_{0-\infty}$ of the tizanidine in the following liquid preparations after being administered to same or similar subject in equivalent doses with respect to tizanidine:
(1) Each 100 mL liquid preparation comprises tizanidine hydrochloride 0.046 g, sodium methylparaben 0.1 g, sodium propylparaben 0.01 g, disodium EDTA 0.1 g, sucralose 0.05 g, citric acid 0.083 g, sodium citrate 0.042 g, strawberry flavoring agent 0.05 g, and the remainder water; or
(2) Each 100 mL liquid preparation comprises tizanidine hydrochloride 0.046 g, sodium methylparaben 0.1 g, sodium propylparaben 0.01 g, 70% sorbitol solution 25 g, disodium EDTA 0.1 g, sucralose 0.05 g, citric acid 0.09 g, sodium citrate 0.035 g, strawberry flavoring agent 0.05 g, and the remainder water; or
(3) Each 100 mL liquid preparation comprises tizanidine hydrochloride 0.046 g, hydroxypropyl cellulose 2.5 g, sodium methylparaben 0.1 g, sodium propylparaben 0.01 g, 70% sorbitol solution 15 g, disodium EDTA 0.1 g, sucralose 0.05 g, citric acid 0.09 g, sodium citrate 0.046 g, strawberry flavoring agent 0.05 g, and the remainder water; or
(4) Each 100 mL liquid preparation comprises tizanidine hydrochloride 0.046 g, hydroxypropyl cellulose 2.5 g, colloidal silicon dioxide 0.5 g, sodium methylparaben 0.1 g, sodium propylparaben 0.01 g, 70% sorbitol solution 15 g, disodium EDTA 0.1 g, sucralose 0.05 g, citric acid 0.09 g, sodium citrate 0.04 g, strawberry flavoring agent 0.05 g, and the remainder water; or
(5) Each 100 mL liquid preparation comprises tizanidine hydrochloride 0.046 g, hydroxypropyl cellulose 5 g, sodium benzoate 0.1 g, glycerin 15 g, 70% sorbitol solution 25 g, disodium EDTA 0.1 g, sucralose 0.05 g, strawberry flavoring agent 0.05 g, and the remainder water.

When the tizanidine liquid preparation of the present disclosure is hermetically stored under the condition of 40° C./75% RH for 0-3 months, the total impurity amount of its related substances is NMT 0.2%, and/or when the tizanidine liquid preparation of the present disclosure is hermetically stored under the condition of 25° C./60% RH for 0-6 months, the total impurity amount of its related substances is ≤0.2%.

In one embodiment, the pre-prandial and post-prandial bioavailability of the liquid preparation of the present disclosure is equivalent with that of Zanaflex® tizanidine tablets. In another embodiment, the post-prandial bioavailability of the liquid preparation of the present disclosure is equivalent with that of Zanaflex® tizanidine capsules.

The evaluation criteria for the bioavailability equivalence of the liquid preparation of the present disclosure and tizanidine tablets/capsules under a pre-prandial or post-prandial condition are:

The 90% confidence interval for $C_{max}$ is between 80%-125%;

The 90% confidence interval for $AUC_{0-t}$ is between 80%-125%;

The 90% confidence interval for $AUC_{0-\infty}$ is between 80%-125%.

The mean value of $T_{max}$ of the tizanidine liquid preparation of the present disclosure under the post-prandial condition is smaller than the mean value of $T_{max}$ of the tizanidine tablets/capsules under the post-prandial condition.

Under the condition that the tizanidine liquid preparation of the present disclosure is administered in the same dose with respect to tizanidine, the incidence of adverse effects of the present disclosure is smaller than the incidence of adverse effects of the tizanidine tablets/capsules.

In one embodiment, under the condition that the tizanidine liquid preparation of the present disclosure is administered in the same dose with respect to tizanidine, the incidence of the pre-prandial adverse effects, e.g., dizziness, or sedation caused by the liquid preparation of the present disclosure is smaller than that of the tizanidine tablets; and/or In another embodiment, the incidence of post-prandial adverse effects, e.g., dizziness, or sedation caused by of the liquid preparation of the present disclosure is smaller than that of the tizanidine tablets/capsules; and/or In another embodiment, the incidence of post-prandial adverse effects—headache of the liquid preparation of the present disclosure is smaller than that of the tizanidine capsules; and/or Use of a tizanidine liquid preparation in preparing a medicament for treating muscle spasm.

There are many factors that affect the chemical stability of medicines, among which temperature is one of the important factors affecting the stability of pharmaceutical preparations. Generally speaking, as the temperature increases, the degradation reaction speed is accelerated. Light is also a reason that may affect the stability of pharmaceutical preparations, wherein light may induce chain reactions, which can accelerate the degradation rate. The presence of oxygen may also accelerate the oxidation reaction, which can affect the stability of the drug. Other factors such as environmental humidity, packaging materials, pH value, excipients and the like may also affect the chemical stability of the drug. The stability of different drugs can be affected by different factors.

In the research process, the preparation researchers of the present disclosure found that the metal ions in the solution have an impact on the chemical stability of the tizanidine solution, in which the presence of the metal ions has the effect of accelerating the degradation of tizanidine related substances. The present disclosure uses disodium EDTA as a chelating agent, which can combine with metal ions in the tizanidine solution to prepare a tizanidine liquid preparation with strong chemical stability and an impurity content of the related substances in compliance with the Pharmacopoeia. Disodium EDTA can combine and maintain with minerals and metal ions such as chromium, iron, lead, mercury, copper, aluminum, nickel, zinc, calcium, cobalt, manganese and magnesium after being dissolved in water. When these minerals and metal ions are combined, they no longer have an impact on the chemical stability of the tizanidine solution, which ensures the chemical stability of the tizanidine liquid preparation of the present disclosure to a great extent.

In some embodiments, the tizanidine liquid preparation of the present disclosure has good chemical stability in both glass bottles and polyethylene terephthalate (PET) bottles which are conventional storage containers for liquid medicines. It can be seen that the present disclosure does not have strict requirements on storage containers, and storage containers can be selected according to actual needs during storage and transportation. The medicinal solution of the present disclosure can be stored at room temperature, which is conducive to reducing the costs of storage and transportation.

In some embodiments, the tizanidine liquid preparation of the present disclosure has a clear appearance, and does not have precipitation, turbidity or other detectable physical changes after being stored for a long time, such as over 30 days, 6 months, 12 months or more than 24 months, which indicates that it has good physical stability. The impurity content of its related substances is far lower than the limit specified by the Pharmacopoeia for the impurity content of the related substances in tizanidine products, which meets the requirements of drug application and can be promoted and applied in clinical practice.

As compared with the existing tizanidine solid preparations on the market, the tizanidine liquid preparation prepared by the present disclosure has less adverse effects in the human body, improving the use safety of the tizanidine drug and the compliance of patients taking the medicine.

In some embodiments, the liquid preparation of the present disclosure is administered via oral cavity, preferably orally administered. It has the advantages of accurate dose titration and convenient administration for young children, the elderly, patients with dysphagia, patients with certain mental illnesses and patients who have difficulty in changing their position in bed.

Meanwhile, as compared with the existing tablets and capsules, the tizanidine liquid preparation prepared by the present disclosure achieves the pre-prandial and post-prandial bioavailability equivalence in human body, and has efficacy which is not smaller than that of the existing solid preparations. Moreover, the impact of food on the action speed of the liquid preparation of the present disclosure is smaller than its impact on the existing solid preparations. As compared with the existing solid preparations, the present disclosure has a faster onset of drug action under a post-prandial condition, and can relieve the pain of patients more quickly.

To sum up, the present disclosure obtains a tizanidine liquid preparation with few impurities, strong chemical and physical stability, and few adverse effects, which achieves pre-prandial and post-prandial bioavailability equivalence with the existing tizanidine solid preparations. Meanwhile, compared with the existing tizanidine solid preparations, the liquid preparation of the present disclosure has a faster onset of drug action under a post-prandial condition, and meets the market demand for tizanidine oral pharmaceutical dosage forms and the clinical needs.

In some embodiments of the present disclosure, a liquid pharmaceutical composition is provided; which contains (a) about 0.1-2 mg/mL of tizanidine hydrochloride, (b) about 0.5-5 mM of EDTA and (c) water, wherein the pH of the liquid pharmaceutical composition is between 3.5 and 6.1, and wherein the liquid pharmaceutical composition retains at least 99% tizanidine concentration as measured by USP assay when stored at room temperature for at least 30 days, or at least 180 days, or at least 12 months, or at least 24 months.

In some embodiments, the liquid pharmaceutical composition further contains d) about 2-6 mM citric acid, and e) about 0.5-3 mM sodium citrate.

In some embodiments, the liquid pharmaceutical composition further contains f) about 2-10 mM of sodium methylparaben; and g) about 0.2-1 mM of sodium propylparaben.

In some embodiments, the liquid pharmaceutical composition further contains about 0.5-5 mM of sucralose.

In some embodiments, the EDTA is disodium EDTA.

In some embodiments, a liquid pharmaceutical composition is provided, which contains (a) about 0.1-2 mg/mL of tizanidine hydrochloride, (b) about 0.5-5 mM of EDTA and (c) water, wherein the pH of the pharmaceutical composition is between 3.5 and 6.1, and wherein the liquid pharmaceutical composition retains at least 95%, or at least 99% tizanidine concentration as measured by USP assay when stored at room temperature for at least 30 days, and wherein the liquid pharmaceutical composition causes less severe side effect in the subject as compared to side effect caused by solid tablets or capsules of tizanidine at the same dosage. In some embodiments, the liquid pharmaceutical composition further contains d) about 2-6 mM citric acid, and e) about 0.5-3 mM sodium citrate. In some embodiments, the liquid pharmaceutical composition further contains f) about 2-10 mM of sodium methylparaben; and g) about 0.2-1 mM of sodium propylparaben. In some embodiments, the liquid pharmaceutical composition further contains h) about 0.5-5 mM of sucralose. In some embodiments, the liquid pharmaceutical composition further contains a flavoring agent, such as a strawberry aromatic agent. In one aspect, the strawberry aromatic agent is present in the pharmaceutical composition at about 0.5 mg/mL.

In some embodiments, the disclosed liquid pharmaceutical composition is administered orally to a subject in need thereof for muscle relaxation. In one aspect, the liquid pharmaceutical composition is administered to the subject either before meal or after meal with the same clinical effect. In other words, the disclosed liquid pharmaceutical composition has the same clinical effect regardless of whether it is administered to the subject before meal or after meal.

In one aspect, same dosage means same amount of active ingredient, which, in this case, is tizanidine. In another aspect, the side effect is selected from the group consisting of headache, dizziness, sedation, and nausea.

In some embodiments, the disclosed liquid pharmaceutical composition causes fewer adverse effects in the subject as compared to adverse effects caused by solid tablets or capsules of tizanidine when administered to the same subject at the same dosage.

In some embodiments, when a single dose of the disclosed liquid pharmaceutical composition is administered to a subject under fasting condition, mean value of Cm is between 4055 and 6336 pg/mL, or between 3751 and 5861 pg/mL, or mean value of $AUC_{0-t}$ is between 11286 and 17635 hr*pg/mL, or between 10200 and 15938 hr*pg/mL, or mean value of $AUC_{0-\infty}$ is between 11752 and 18362 hr*pg/mL or between 10655 and 16648 hr*pg/mL. In some embodiments, the $C_{max}$, $AUC_{0-t}$, and $AUC_{0-\infty}$ is each within the range of 80%-125% of the mean value of $C_{max}$, mean value of $AUC_{0-t}$ and mean value of $AUC_{0-\infty}$ of the tizanidine in Zanaflex® tizanidine tablet or capsules.

In some embodiments, when a single dose of the disclosed liquid pharmaceutical composition is administered to a subject under fed condition, mean value of $C_{max}$ is between 4378 and 6841 pg/mL, or between 4092 and 6395 pg/mL, or mean value of $AUC_{0-t}$ is between 15404 and 24070 hr*pg/mL, or between 13983 and 21848 hr*pg/mL, or mean value of $AUC_{0-\infty}$ is between 15807 and 24698 hr*pg/mL or between 14379 and 22467 hr*pg/mL. In some embodiments, the $C_{max}$, $AUC_{0-t}$, and $AUC_{0-\infty}$ is each within the range of 80%-125% of the mean value of $C_{max}$, mean value of $AUC_{0-t}$ and mean value of $AUC_{0-\infty}$ of the tizanidine in Zanaflex® tizanidine tablet or capsules.

In some embodiments, tizanidine hydrochloride is present at a concentration of 0.046 g/100 mL in the disclosed pharmaceutical composition, wherein when the liquid preparation is stored at room temperature for at least 30 days, or at least 6 months, or at least 12 months, or at least 24 months, the total impurity is 0.2%, and wherein after the liquid pharmaceutical composition is administered to a subject, the mean value of $C_{max}$, mean value of $AUC_{0-t}$ and/or mean value of $AUC_{0-\infty}$ of tizanidine thereof are each within the range of 80%-125% of the mean value of $C_{max}$, mean value of $AUC_{0-t}$ and/or mean value of $AUC_{0-\infty}$ of the tizanidine in the following liquid preparations after being administered in equivalent doses with respect to tizanidine:

(1) each 100 mL liquid preparation comprises tizanidine hydrochloride 0.046 g, sodium methylparaben 0.1 g, sodium propylparaben 0.01 g, disodium EDTA 0.1 g, sucralose 0.05 g, citric acid 0.083 g, sodium citrate 0.042 g, strawberry aromatic agent 0.05 g, and the remainder water; or (2) each 100 mL liquid preparation comprises tizanidine hydrochloride 0.046 g, sodium methylparaben 0.1 g, sodium propylparaben 0.01 g, 70% sorbitol solution 25 g, disodium EDTA 0.1 g, sucralose 0.05 g, citric acid 0.09 g, sodium citrate 0.035 g, strawberry aromatic agent 0.05 g, and the remainder water; or, (3) each 100 mL liquid preparation comprises tizanidine hydrochloride 0.046 g, hydroxypropyl cellulose 2.5 g, sodium methylparaben 0.1 g, sodium propylparaben 0.01 g, 70% sorbitol solution 15 g, disodium EDTA 0.1 g, sucralose 0.05 g, citric acid 0.09 g, sodium citrate 0.046 g, strawberry aromatic agent 0.05 g, and the remainder water; or (4) each 100 mL liquid preparation comprises tizanidine hydrochloride 0.046 g, hydroxypropyl cellulose 2.5 g, colloidal silicon dioxide 0.5 g, sodium methylparaben 0.1 g, sodium propylparaben 0.01 g, 70% sorbitol solution 15 g, disodium EDTA 0.1 g, sucralose 0.05 g, citric acid 0.09 g, sodium citrate 0.04 g, strawberry aromatic agent 0.05 g, and the remainder water; or (5) each 100 mL liquid preparation comprises tizanidine hydrochloride 0.046 g, hydroxypropyl cellulose 5 g, sodium benzoate 0.1 g, glycerin 15 g, 70% sorbitol solution 25 g, disodium EDTA 0.1 g, sucralose 0.05 g, strawberry aromatic agent 0.05 g, and the remainder water.

DETAILED DESCRIPTION

The technical solutions of the present disclosure will be described below in greater details with reference to the embodiments of the present disclosure. The described embodiments are only a part of the preferred embodiments of the present disclosure, rather than all the embodiments. Based on the embodiments of the present disclosure, all other embodiments obtained by those of ordinary skill in the art without creative efforts shall fall within the protection scope of the present disclosure.

In some embodiments, the present disclosure provides a stable tizanidine liquid preparation, wherein the active pharmaceutical ingredient of the liquid preparation is one or more of tizanidine or a pharmaceutically acceptable salt, solvate and hydrate thereof. The term stable according to the present disclosure refers to chemically stable and/or physically stable.

Regardless of the presenting form of the active pharmaceutical ingredient of the present disclosure, after it is dissolved, it is the tizanidine dissolved in the drug solution that produces the medicinal effect. In order to facilitate data comparison, in the embodiments of the present disclosure, tizanidine hydrochloride was preferably used as the bulk drug to investigate various aspects.

The range of pH value of bulk drug solution of tizanidine hydrochloride was investigated:

Experimental Method:
(1) 0.323 g of tizanidine hydrochloride was weighed and dissolved in 400 mL of purified water;
(2) The solution of the previous step was divided into four equal parts, and the pH was adjusted to 3.5, 4.5, 5.5 and 6.5 using 0.1N HCl and 0.1N NaOH;
(3) Freezing and thawing test-four sample solutions were stored at 2-8° C., room temperature, and 40° C./75% RH respectively for 24 hours, which was repeated 3 times.

The changes in the pH and appearance of the tizanidine hydrochloride bulk drug solution

TABLE 1

Table of investigation of effect of pH on tizanidine hydrochloride bulk drug solution

| Sample | pH value | Appearance |
|---|---|---|
| 1 | 3.5 | Clear colorless solution |
| 2 | 4.5 | Clear colorless solution |
| 3 | 5.5 | Clear colorless solution |
| 4 | 6.5 | Clear pale yellow solution |

Physical observation showed that when the pH was 6.5, the color of the solution changed from colorless to pale yellow.

Therefore, in some embodiments, the pH value of the present disclosure is preferably selected to be greater than 3.5 and smaller than 6.5.

Next, the stability of the tizanidine liquid preparation of the present disclosure is investigated through specific examples.

Glass bottle/polyethylene terephthalate (PET) is one of the inner packaging's commonly used for solid tablets or liquid preparations. The glass bottle has excellent properties such as good heat resistance and uneasy adsorption, but it is relatively brittle, easy to be broken, and cannot be pressed, which brings inconvenience to the production and transportation, and the trace amount of metal ions contained in glass may affect the stability of drugs. The PET bottle is not easy to be broken, has zero breakage rate, low price, and low cost of production and transportation, but its heat resistance is poor, and more additives are added in the production process thereof, easily leading to changes in the quality of drugs. Moreover, the PET bottle also has disadvantages of breathability, easy adsorption and the like, which can also accelerate the speed of oxidative deterioration of drugs and cause drug deterioration.

Therefore, during the stability investigation process of the present disclosure, the tizanidine liquid preparation was stored in a glass bottle and a PET bottle, which are two commonly used medicine storage containers, to detect the related substances.

The test method of stability investigation of the present disclosure is:
a Accelerated Test Steps:
(1) In the stability test chamber, the temperature was set to 40° C. and the relative humidity was set to 75%;
(2) The liquid preparations sealed into a glass bottle and the liquid preparations sealed into a PET bottle were taken and placed in a preset stability test chamber;
(3) The samples after placement were taken to detect the related substances.
b Normal Temperature Test Steps:
(1) In the stability test chamber, the temperature was set to 25° C. and the relative humidity was set to 60%;
(2) The liquid preparations sealed into a glass bottle and the liquid preparations sealed into a PET bottle were taken and placed in a preset stability test chamber;
(3) The samples after placement were taken to detect the related substances.

This method was adopted for the test methods of the accelerated test and the normal temperature test in all the examples of the present disclosure.

Example 1

In addition to the tizanidine bulk drug, the liquid preparation of the present disclosure also comprises disodium EDTA and one or more other pharmaceutically acceptable excipients. Therefore, after the relevant excipients were added to make the tizanidine hydrochloride liquid preparation, the stability and range of pH value of the liquid preparation were studied:

(I) Experimental Formula:

TABLE 2

Formula table

| Material name | 1 Unit measurement (g/1000 mL) | 2 Unit measurement (g/1000 mL) | 3 Unit measurement (g/1000 mL) |
|---|---|---|---|
| Tizanidine hydrochloride | 0.46 | 0.46 | 0.46 |
| Sodium methylparaben | 1.00 | 1.00 | 1.00 |
| Sodium propylparaben | 0.10 | 0.10 | 0.10 |
| Disodium EDTA | 1.00 | 1.00 | 1.00 |
| Sucralose | 0.50 | 0.50 | 0.50 |
| Citric acid | 1.66 | 0.83 | 0.83 |
| Sodium citrate | 0.42 | 0.42 | 3.70 |
| Strawberry flavoring agent | 0.50 | 0.50 | 0.50 |
| 0.1NHCl | Adjusting pH to about 4.0 | — | — |
| 0.1NNaOH | — | — | Adjusting pH to about 6.0 |
| Purified water (appropriate amount) | Making up to 1000 mL | Making up to 1000 mL | Making up to 1000 mL |

With regard to the formula table of the present application, it should be understood that the invention disclosed in the present application is not limited to a specific preparation volume. In the case where the concentration of each component of the liquid preparation is determined, the preparation volume can be changed according to the requirements of production and test.

Descriptions of liquid preparation volumes provided throughout this application are given for the purpose of describing particular embodiments or concentration of each component only, and are not intended to limit the scope of the present disclosure.

(II) Process:

The materials were weighed according to the prescribed amount for use;

(1) Disodium EDTA was dissolved in an appropriate amount of water and stirred well;
(2) Sucralose was dissolved in an appropriate amount of water, added to the solution obtained in step (1), and stirred evenly;
(3) Sodium methylparaben was dissolved in an appropriate amount of water, and the mixture was added to the solution obtained in step (2), and stirred evenly;
(4) Sodium propylparaben was dissolved in an appropriate amount of water, and the mixture was added to the solution obtained in step (3), and stirred evenly;
(5) Citric acid was dissolved in an appropriate amount of water, and the mixture was added to the solution obtained in step (4), and stirred evenly;
(6) Sodium citrate was dissolved in an appropriate amount of water, and the mixture was added to the solution obtained in step (5), and stirred evenly;
(7) Tizanidine hydrochloride was dissolved in an appropriate amount of water, and the mixture was added to the solution obtained in step (6), and stirred evenly;
(8) The pH of the solution in step (7) was adjusted to about 4.0 or 6.0 using 0.1N HCl or 0.1N NaOH or no pH adjustment was performed.
(9) Strawberry flavoring agent was added to the solution obtained in step (8) under stirring, and stirred evenly;
(10) Water was added to adjust the volume to 1000 mL, and the obtained solution was filtered to obtain a tizanidine hydrochloride liquid preparation.

(III) Detection Methods for the Related Substances:

The related substances were determined using high performance liquid chromatography.

Test solution: About 10 g of tizanidine hydrochloride liquid preparation was taken, accurately weighed (corresponding to about 4 mg of tizanidine), and put in a 100 mL volumetric flask. The preparation was diluted to the mark by adding a diluent [a mixture of mobile phase A and mobile phase B according to a certain ratio]. The mixture was shaken well, and filtered to take the filtrate.

Control solution: 1.0 mL of the test solution was precisely measured, put in a 100 mL volumetric flask. The test solution was diluted to the mark by adding a diluent. The mixture was shaken well.

The chromatographic column was an octadecylsilane-bonded silica gel column C18 (4.6×250 mm, 5 μm). Gradient elution was performed according to Table 3 in which the sodium pentanesulfonate solution (3.5 g of sodium pentanesulfonate was taken and dissolved in 1000 mL of water, and the pH was adjusted to 3.0 using phosphoric acid solution or sodium hydroxide test solution) was used as mobile phase A, and acetonitrile was used as mobile phase B; the flow rate was 1.0 mL/min; the detection wavelength was 230 nm; the injection volume was 50 μL; the column temperature was 30° C.

TABLE 3

Gradient elution procedure

| Time (min) | Mobile phase A(%) | Mobile phase B (%) |
|---|---|---|
| 0 | 94 | 6 |
| 5 | 94 | 6 |
| 20 | 80 | 20 |
| 25 | 78 | 28 |
| 45 | 72 | 45 |
| 50 | 55 | 50 |
| 55 | 50 | 50 |
| 60 | 94 | 6 |
| 0 | 94 | 6 |

Limit: If there are impurity peaks in the chromatogram of the test solution, the total area of the impurity peaks shall not be greater than 0.5 times of the main peak area of the control solution (i.e., the total impurity amount of the related substances shall not exceed 0.5%).

This detection method can be used for the detection of the related substances in all the examples in the present specification, but the detection method of the related substances of the present disclosure is not limited to this detection method; those skilled in the art can also partly adjust the detection method/detection parameters by conventional means to detect the related substances of the present disclosure.

TABLE 4

Detection results of the related substances of tizanidine hydrochloride liquid preparations with different pH in the accelerated test

| | | | PET Bottle | |
|---|---|---|---|---|
| Sample | Condition | 0 Day | 1 M 40° C./ 75% RH | 3 M 40° C./ 75% RH |
| 1. | pH | 4.03 | 4.09 | 4.11 |
| | Assay of Tizanidine (%) | 98.8 | 99.3 | 100.7 |
| | Total Impurity (%) | 0.01 | 0.02 | 0.05 |
| 2. | pH | 5.04 | 5.04 | 5.05 |
| | Assay of Tizanidine (%) | 100.6 | 99.2 | 100.5 |
| | Total Impurity (%) | 0.02 | 0.03 | 0.05 |
| 3. | pH | 6.00 | 6.07 | 6.02 |
| | Assay of Tizanidine (%) | 99.2 | 98.5 | 100.4 |
| | Total Impurity (%) | 0.01 | 0.08 | 0.16 |

The results in Table 4 show that under the accelerated condition, when the pH was 4.0/5.0/6.1, the total impurity content of the related substances in tizanidine liquid preparations for 0 day, 1 month (1M), and 3 months (3M) were all less than 0.2%, which was far less than the 0.5% stipulated in the Pharmacopoeia; meanwhile, no turbidity or precipitation occurred in liquid preparations with different pH values. It can be seen that when the pH of the tizanidine liquid preparation of the present disclosure changes within the range of 4.0-6.1, the pH value has no substantial effect on the physical and chemical stability of the preparation, and will not affect the marketing and use of the drug.

In order to further verify the long-term stability of the liquid preparation in this example, the tizanidine liquid preparation prepared in this example was subjected to a normal temperature test. In order to save resources, only the No. 2 formula without HCl or NaOH added in Table 2 was investigated in this investigation.

TABLE 5

Detection results of the related substances of tizanidine hydrochloride liquid preparation of No. 2 formula in normal temperature test

| Condition | Room temperature for 6 months-25° C./60% RH PET bottle |
|---|---|
| Content % | 101.2 |
| Total impurity of the related substances % | 0.03 |

The total impurities of the related substances in the liquid preparation of this example which was placed at room temperature for 6 months were 0.03% (PET bottle), wherein the total impurity content of the related substances were less than 0.2%, far less than the limit of 0.5% stipulated in the Pharmacopoeia, indicating that the liquid preparation of this example had good chemical stability.

There was no big difference in the detection results of the related substances in the liquid preparation of this example stored in the glass bottle and the PET bottle. It can be seen that the liquid preparation of this example did not have strict requirements on storage containers, and storage containers can be selected according to actual needs during storage and transportation.

Meanwhile, whether in the accelerated test or in the normal temperature test, the tizanidine liquid preparation of this example did not appear precipitation, turbidity or other phenomena, indicating that the liquid preparation of this example had good physical stability under both accelerated conditions and normal temperature conditions for a long-term storage.

It can be seen that the liquid preparation of this example not only had low impurity content, but also had good chemical/physical stability, which meets the specifications of the Pharmacopoeia and the requirements for drug marketing, and has strong durability to storage containers, providing a variety of storage options clinically.

Example 2

In this example, an excipient-co-solvent was added to the formula to investigate the stability.

(I) Experimental Formula

TABLE 6

Formula table

| Material name | Role in formula | Unit measurement (g/1000 mL) |
|---|---|---|
| Tizanidine hydrochloride | Active ingredient | 0.46 |
| Sodium methylparaben | Preservative | 1.00 |
| Sodium propylparaben | Preservative | 0.10 |
| 70% sorbitol | Co-solvent | 250.00 |
| Disodium EDTA | Chelating agent | 1.00 |
| Sucralose | Sweetening agent | 0.50 |
| Citric acid | pH adjusting agent | 0.90 |
| Sodium citrate | pH adjusting agent | 0.35 |
| Strawberry flavoring agent | flavoring agent | 0.50 |
| Purified water (appropriate amount) | Diluent | Making up to 1000 mL |

(II) Process:

The materials were weighed according to the prescribed amount for use;

(1) Disodium EDTA was dissolved in an appropriate amount of water and stirred well;
(2) Sucralose was dissolved in an appropriate amount of water, and the mixture was added to the solution obtained in step (1);
(3) Under stirring, sorbitol with a concentration of 70% was added to the solution obtained in step (2);
(4) Sodium methylparaben and sodium propylparaben were dissolved in water, and the mixture was added to the solution obtained in step (3) under stirring;
(5) Citric acid and sodium citrate were added to the solution obtained in step (4) under stirring;
(6) Tizanidine hydrochloride was dissolved in water alone, then the mixture was added to the solution obtained in step (5) under continuous stirring;
(7) Strawberry flavoring agent was added to the solution obtained in step (6) under stirring;
(10) Water was added to adjust the volume to 1000 mL, and the obtained solution was filtered to obtain a tizanidine hydrochloride liquid preparation.

(III) Stability Investigation

The liquid preparations prepared in this example were subjected to accelerated test.

TABLE 7

Detection results of the related substances in accelerated test

| Condition | 0 day | Accelerated for 1 month-40° C./75% RH | | Accelerated for 3 months-40° C./75% RH | |
|---|---|---|---|---|---|
| | | Glass bottle | PET bottle | Glass bottle | PET bottle |
| Content % | 101.4 | 101.5 | 104.8 | 101.4 | 101.7 |
| Total impurity of the related substances % | Undetected | Undetected | Undetected | 0.15 | 0.16 |

At 0 day, the pH value of the liquid preparation of this example was measured to be 5.0. Since when the pH value of the tizanidine liquid preparation of the present disclosure changes within the range of 4.0-6.1, the stability of the present disclosure is not substantially affected, the pH value was not investigated in this example.

Under accelerated conditions, the total impurity content of the related substances in the liquid preparation of this example in 0, 1, and 3 months was all less than 0.2%, far less than the limit of 0.5% specified by the Pharmacopoeia, indicating the liquid preparation of this example had good chemical stability, and complied with regulations of the Pharmacopoeia.

In order to further verify the long-term stability of the liquid preparation of this example, the tizanidine liquid preparations prepared in this example were subjected to normal temperature test.

TABLE 8

Detection results of the related substances in normal temperature test

| Condition | Room temperature for 6 months-25° C./60% RH | |
|---|---|---|
| | Glass bottle | PET bottle |
| Content % | 102.3 | 106.0 |
| Total impurity of the related substances % | 0.15 | 0.19 |

The total impurities of the related substances in the liquid preparation of this example placed at room temperature for 6 months were 0.15% (glass bottle) and 0.19% (PET bottle), which were both less than 0.2%, far less than the limit of 0.5% specified in the Pharmacopoeia, indicating that the liquid preparation of this example had good chemical stability, and complied with regulations of the Pharmacopoeia.

There was no significant difference in the detection results of the total impurity of the related substances in the liquid preparation of this example stored in the glass bottle and the PET bottle. It can be seen that the liquid preparation of this example did not have strict requirements on storage containers, and storage containers can be selected according to actual needs during storage and transportation.

Meanwhile, whether in the accelerated test or in the normal temperature test, the tizanidine liquid preparation of this example did not appear precipitation, turbidity or other phenomena, indicating that the liquid preparation of this example had good physical stability under both accelerated conditions and normal temperature conditions for a long-term storage.

The liquid preparation of this example not only had low impurity content, but also had good long-term stability, which meets the requirements of the Pharmacopoeia and the requirements for drug marketing.

Compared with Example 1, in this example, a co-solvent was added to the formula of the liquid preparation. It can be seen that the addition of the co-solvent has no substantial effect on the physical and chemical stability of the liquid preparation of the present disclosure, and will not affect the marketing and use of the drug.

Example 3

In this example, an excipient-thickening agent was added to the formula, and the addition amount of the co-solvent was adjusted to investigate the stability.

(I) Experimental Formula

TABLE 9

Formula table

| Material name | Role in formula | Unit measurement (g/1000 mL) |
|---|---|---|
| Tizanidine hydrochloride | Active ingredient | 0.46 |
| Hydroxypropyl cellulose | Thickening agent | 25.00 |
| Sodium methylparaben | Preservative | 1.00 |
| Sodium propylparaben | Preservative | 0.10 |
| 70% sorbitol | Co-solvent | 150.00 |
| Disodium EDTA | Chelating agent | 1.00 |
| Sucralose | Sweetening agent | 0.50 |
| Citric acid | pH adjusting agent | 0.90 |
| Sodium citrate | pH adjusting agent | 0.46 |
| Strawberry flavoring agent | Flavoring agent | 0.50 |
| Purified water (appropriate amount) | Diluent | Making up to 1000 mL |

(II) Process

The materials were weighed according to the prescribed amount for use;

(1) Hydroxypropyl cellulose was added to an appropriate amount of water to disperse, and stirred until the solution became clear.

(2) Disodium EDTA was dissolved in water and the mixture was added to the solution obtained in step (1) under stirring.

(3) Sorbitol with a concentration of 70% was added to the solution obtained in step (2) under stirring, and stirred until the solution became clear.

(4) Sodium methylparaben and sodium propylparaben were dissolved in water, and the mixture was added to the solution obtained in step (3) under stirring.

(5) Citric acid and sodium citrate were added to the solution obtained in step (4) with stirring.

(6) Sucralose was dissolved in water, and the mixture was added to the solution obtained in step (5) under stirring.

(7) Tizanidine hydrochloride was dissolved in water alone, then the mixture was added to the solution obtained in step (6) under continuous stirring.

(8) Strawberry flavoring agent was added to the solution obtained in step (7) under continuous stirring.

(9) Water was added to adjust the volume to 1000 mL, and the obtained solution was filtered to obtain a tizanidine hydrochloride liquid preparation.

(III) Stability Investigation

The liquid preparations prepared in this example were subjected to accelerated test.

TABLE 10

Detection results of the related substances in accelerated test

| Condition | O day | Accelerated for 1 month-40° C./75% RH | | Accelerated for 3 months-40° C./75% RH | |
|---|---|---|---|---|---|
| | | Glass bottle | PET bottle | Glass bottle | Polyester bottle |
| Content % | 103.8 | 100.7 | 101.5 | 102.5 | 102.4 |
| Total impurity of the related substances % | Undetected | Undetected | Undetected | 0.12 | 0.10 |

At 0 day, the pH value of the liquid preparation of this example was measured to be 5.2. Since when the pH value of the tizanidine liquid preparation of the present disclosure changes within the range of 4.0-6.1, the stability of the present disclosure is not substantially affected, the pH value was not investigated in this example.

Under accelerated conditions, the total impurity content of the related substances in the liquid preparation of this example in 0, 1, and 3 months was all less than 0.2%, far less than the limit of 0.5% specified by the Pharmacopoeia, indicating the liquid preparation of this example had good chemical stability, and complied with regulations of the Pharmacopoeia.

In order to further verify the long-term stability of the liquid preparation of this example, the tizanidine liquid preparation prepared in this example was subjected to normal temperature test.

TABLE 11

Detection results of the related substances in normal temperature test

| Condition | Room temperature for 6 months-25° C./60% RH | |
| --- | --- | --- |
| | Glass bottle | PET bottle |
| Content % | 104.3 | 104.3 |
| Total impurity of the related substances % | 0.06 | 0.06 |

The total impurities of the related substances in the liquid preparation of this example placed at room temperature for 6 months were 0.06% (glass bottle) and 0.06% (PET bottle), which were both less than 0.2%, far less than the limit of 0.5% specified in the Pharmacopoeia, indicating that the liquid preparation of this example had good chemical stability, and complied with regulations of the Pharmacopoeia.

There was no significant difference in the detection results of the total impurity of the related substances in the liquid preparation of this example stored in the glass bottle and the PET bottle. It can be seen that the liquid preparation of this example did not have strict requirements on storage containers, and storage containers can be selected according to actual needs during storage and transportation.

Meanwhile, whether in the accelerated test or in the normal temperature test, the tizanidine liquid preparation of this example did not have precipitation, turbidity or other detectable changes, indicating that the liquid preparation of this example had good physical stability under both accelerated conditions and normal temperature conditions for a long-term storage.

The liquid preparation of this example not only had low impurity content, but also had good long-term stability, which meets the specifications of the Pharmacopoeia and the requirements for drug marketing.

Compared with Example 2, in this example, a thickening agent was added, and the addition amount of the co-solvent was reduced. It can be seen that the changes of the viscosity of the liquid preparation and the adjustment of the addition amount of the co-solvent in the present disclosure have no substantial effect on the physical and chemical stability of the liquid preparation of the present disclosure, and will not affect the marketing and use of the drug.

Example 4

In this example, the type and addition amount of the thickening agent in the formula were adjusted to investigate the stability.

(I) Experimental Formula

TABLE 12

Formula table

| Material name | Role in formula | Unit measurement (g/1000 mL) |
| --- | --- | --- |
| Tizanidine hydrochloride | Active ingredient | 0.46 |
| Hydroxypropyl cellulose | Thickening agent | 25.00 |
| Colloidal silicon dioxide | Thickening agent | 5.0 |
| Sodium methylparaben | Preservative | 1.0 |
| Sodium propylparaben | Preservative | 0.1 |
| 70% sorbitol | Co-solvent | 150.00 |
| Disodium EDTA | Chelating agent | 1.00 |
| Sucralose | Sweetening agent | 0.50 |
| Citric acid | pH adjusting agent | 0.90 |
| Sodium citrate | pH adjusting agent | 0.40 |
| Strawberry flavoring agent | Flavoring agent | 0.50 |
| Purified water (appropriate amount) | Diluent | Making up to 1000 mL |

(II) Process

The materials were weighed according to the prescribed amount for use;

(1) Hydroxypropyl cellulose was added to an appropriate amount of water to disperse, and stirred until the solution became clear.

(2) Disodium EDTA was dissolved in water and the mixture was added to the solution obtained in step (1) under stirring, and stirred until the solution became clear.

(3) Sorbitol with a concentration of 70% was added to the solution obtained in step (2) under stirring, and stirred until the solution became clear.

(4) Sodium methylparaben and sodium propylparaben were dissolved in water, and the mixture was added to the solution obtained in step (3) under stirring.

(5) Citric acid and sodium citrate were dissolved in water, and the mixture was added to the solution obtained in step (4) with stirring.

(6) Sucralose was dissolved in water, and the mixture was added to the solution obtained in step (5).

(7) Colloidal silicon dioxide was dispersed in water and the mixture was added to the solution obtained in step (6) with stirring.

(8) Tizanidine hydrochloride was dissolved in water alone, then the mixture was added to the solution obtained in step (7) under continuous stirring.

(9) Strawberry flavoring agent was added to the solution obtained in step (8) under continuous stirring.

(10) Water was added to adjust the volume to 1000 mL, and the obtained solution was filtered to obtain a tizanidine hydrochloride liquid preparation.

(III) Stability investigation

The liquid preparations prepared in this example were subjected to accelerated test.

TABLE 13

Detection results of the related substances in accelerated test

| Condition | 0 day | Accelerated for 1 month-40° C./75% RH | | Accelerated for 3 months-40° C./75% RH | |
|---|---|---|---|---|---|
| | | Glass bottle | PET bottle | Glass bottle | PET bottle |
| Content % | 102.2 | 101.2 | 101.4 | 102.9 | 101.7 |
| Total impurity of the related substances % | Undetected | Undetected | Undetected | 0.08 | 0.09 |

At 0 day, the pH value of the liquid preparation of this example was measured to be 5.1. Since when the pH value of the tizanidine liquid preparation of the present disclosure changes within the range of 4.0-6.1, the stability of the present disclosure is not substantially affected, the pH value was not investigated in this example.

Under accelerated conditions, the total impurity content of the related substances in the liquid preparation of this example in 0, 1, and 3 months was all less than 0.2%, far less than the limit of 0.5% specified by the Pharmacopoeia, indicating the liquid preparation of this example had good chemical stability, and complied with regulations of the Pharmacopoeia.

On the basis of Example 3, the formula of this example was added with colloidal silicon dioxide to adjust the formula of the thickening agent. According to the comparison of the detection results of the total impurities of the related substances in Table 10 and Table 13, it can be seen that the changes of the formula of the thickening agent had no substantial effect on the chemical stability of the present disclosure; and according to the comparison results of Table 7/Table 10 and Table 13, it can be seen that the chemical stability of the tizanidine liquid preparation of this example was obviously not lower than that of the tizanidine liquid preparation of Example 2/Example 3. Under accelerated conditions, the impurity content of the related substances of the tizanidine liquid preparation of this example in 0-3 months complied with the regulations of the Pharmacopoeia.

There was no big difference in the detection results of the related substances in the liquid preparation of this example stored in the glass bottle and the PET bottle. It can be seen that the liquid preparation of this example did not have strict requirements on storage containers, and storage containers can be selected according to actual needs during storage and transportation.

Meanwhile, the liquid preparation of this example did not appear precipitation, turbidity or other phenomena, which had good physical stability.

It can be seen that the adjustment of the formula of the thickening agent has no substantial effect on the physical and chemical stability of the liquid preparation of the present disclosure, and will not affect the marketing and use of the drug.

Example 5

In this example, the adjustment of excipients was intensified to investigate the stability.

(I) Experimental Formula

TABLE 14

Formula table

| Material name | Role in formula | Unit measurement (g/1000 mL) |
|---|---|---|
| Tizanidine hydrochloride | Active ingredient | 0.46 |
| Hydroxypropyl cellulose | Thickening agent | 50.0 |
| Sodium benzoate | Preservative | 1.0 |
| Glycerin | Sweetening agent | 150.0 |
| 70% sorbitol | Co-solvent | 250.0 |
| Disodium EDTA | Chelating agent | 1.0 |
| Sucralose | Sweetening agent | 0.5 |
| Strawberry flavoring agent | Flavoring agent | 0.5 |
| Purified water (appropriate amount) | Diluent | Making up to 1000 mL |

(II) Process

The materials were weighed according to the prescribed amount for use;

(1) Hydroxypropyl cellulose was added to an appropriate amount of water to disperse, and stirred until the solution became clear.
(2) Sodium benzoate was dissolved in water and the mixture was added to the solution obtained in step (1).
(3) Then disodium EDTA was dissolved in water and the mixture was added to the solution obtained in step (2) under stirring.
(4) Sucralose was added to the solution obtained in step (3) and stirred evenly.
(5) Glycerin was added to the solution obtained in step (4).
(6) Sorbitol with a concentration of 70% was added to the solution obtained in step (5) under stirring.
(7) Tizanidine hydrochloride was dissolved in water alone, then the mixture was added to the solution obtained in step (6) under continuous stirring.
(8) Strawberry flavoring agent was added to the solution obtained in step (7) under continuous stirring.
(9) Water was added to adjust the volume to 1000 mL, and the obtained solution was filtered to obtain a tizanidine hydrochloride liquid preparation.

(III) Stability investigation

The liquid preparations prepared in this example were subjected to accelerated test.

TABLE 15

Detection results of the related substances in accelerated test

| Condition | O day | Accelerated for 1 month at 40° C./75% RH | | Accelerated for 3 months at 40° C./75% RH | |
| --- | --- | --- | --- | --- | --- |
| | | Glass bottle | PET bottle | Glass bottle | PET bottle |
| Content % | 97.9 | 97.8 | 98.5 | 101.8 | 101.4 |
| Total impurity of the related substances % | Undetected | Undetected | Undetected | Undetected | Undetected |

Under accelerated conditions, the total impurities of the related substances in this example were not detected in 0, 1, and 3 months. The total impurity content was all less than 0.2%, far less than the limit of 0.5% stipulated in the Pharmacopoeia, indicating the liquid preparation of this example had good chemical stability, and complied with regulations of the Pharmacopoeia.

There was no difference in the detection results of the related substances of this example stored in the glass bottle and the PET bottle. It can be seen that this example did not have strict requirements on the storage containers, and the storage containers can be selected according to actual needs during storage and transportation.

Meanwhile, the tizanidine liquid preparation of this example did not have precipitation, turbidity or other phenomena, indicating that it has good physical stability.

Compared with the formula of Example 2, the pH value adjusting agent was deleted in this example. The pH value of the medicinal solution in this example was detected to be 4.9 at 0 day, which was within the pH value range of 4.0-6.1. According to the comparison results of the total impurities of the related substances in this example and Example 2 under the accelerated test (comparing Table 15 with Table 7), it can be seen that the deletion of the pH value adjusting agent had no substantial effect on the physical and chemical stability of the liquid preparation of the present disclosure, and will not affect the marketing and use of the drug.

In this example, the preservative in the formula of Example 2 was replaced with sodium benzoate. According to the comparison results of the total impurities of the related substances in this example and Example 2 under the accelerated test (comparing Table 15 with Table 7), it can be seen that the replacement of the preservative had no substantial impact on the physical and chemical stability of the liquid preparation of the present disclosure, and will not affect the marketing and use of the drug.

As compared with the formula of Example 2, glycerin was added as a sweetening agent in this example. According to the comparison results of the total impurities of the related substances in this example and Example 2 under the accelerated test (comparing Table 15 with Table 7), it can be seen that the change of the sweetening agent formula had no substantial impact on the physical and chemical stability of the liquid preparation of the present disclosure, and will not affect the marketing and use of the drug.

As compared with the formula of Example 2, hydroxypropyl cellulose was added as a thickening agent in this example. According to the comparison results of the total impurities of the related substances in this example and Example 2 under the accelerated test (comparing Table 15 with Table 7), it can be seen that the addition of the thickening agent had no substantial impact on the physical and chemical stability of the liquid preparation of the present disclosure, and will not affect the marketing and use of the drug.

Compared with the formula of Example 2, in the formula of this example, in addition to the active substance tizanidine hydrochloride, only the excipients sorbitol, disodium EDTA, and sucralose and strawberry flavoring agent which only play a role in correcting the taste were retained, the rest of the excipients were all different. It can be seen that in addition to sorbitol and disodium EDTA, corresponding changes and deletions of other excipients within the scope of knowledge of those skilled in the art have no substantial impact on the physical and chemical stability of the liquid preparation of the present disclosure, and will not affect the marketing and use of the drug.

Meanwhile, according to the comparison between Example 1 and Example 2, it can be seen that the addition of co-solvent-sorbitol had no substantial effect on the physical and chemical stability of the liquid preparation of the present disclosure, and will not affect the marketing and use of the drug.

It can be seen that the changes and deletions of other excipients other than disodium EDTA in the present disclosure will not have a substantial impact on the physical and chemical stability of the present disclosure. The other excipients comprise but are not limited to:

a pH adjusting agent (citric acid, ascorbic acid, acetic acid, tartaric acid, trisodium citrate, sodium citrate, potassium citrate, sodium phosphate, tricalcium phosphate, calcium carbonate, sodium bicarbonate, calcium phosphate, calcium carbonate, magnesium hydroxide, hydrochloric acid, sodium hydroxide, etc.); and/or a co-solvent (sorbitol, maltitol, mannitol, isomaltose, xylitol, glucose, fructose, etc.); and/or a preservative (sodium benzoate, ethylparaben, propylparaben, sodium methylparaben, sodium ethylparaben, sodium propylparaben, benzoic acid, potassium phenylpropionate, sorbic acid, sodium sorbate, calcium sorbate, potassium sorbate, dehydroacetic acid, sodium diacetate, calcium propionate, etc.); and/or a thickening agent (hypromellose, hydroxypropyl cellulose, colloidal silicon dioxide, methylcellulose, sodium carboxymethylcellulose, sodium alginate, cyclodextrin, etc.); and/or a flavoring agent (strawberry flavoring agent, orange flavoring agent, banana flavoring agent, cherry flavoring agent, lemon flavoring agent, cardamom flavoring agent, fennel flavoring agent, mint flavoring agent, menthol flavoring agent, vanillin flavoring agent, etc.); and/or a sweetening agent (sucralose, glycerin, sodium saccharin, glucose, stevia, stevioside, aspartame, cyclamate, acesulfame potassium, alitame, neotame, etc.); and/or a coloring agent for color-enhancing effect only (amaranth red, carmine, erythrosine, new red, lemon yellow, sunset yellow, indigo, beet red, shellac red, bilberry red, capsicum red, red rice red, etc.).

The investigation time designed for the stability research of the tizanidine liquid preparation of the present disclosure was 24 months or longer. At present, the data of the 0-3 month accelerated test and the 0-6 month normal temperature test of the tizanidine liquid preparation of the present disclosure show that the impurity content of the related substances thereof was all less than 0.2% at 40° C./75% RH and 25° C./60% RH, which was far less than the limit of 0.5% stipulated in the Pharmacopoeia. This shows that the stability of the liquid preparation of the present disclosure under the medicine storage conditions can be expected to be comparable to the stability obtained in the above-described stability test.

The tizanidine liquid preparation of the present disclosure was added with a preservative to investigate the efficacy of the preservative and the stability of 24 months or longer. It can be expected that the microbial indicators of the liquid preparation of the present disclosure meet the quality standards of medicines.

Example 6

In the present disclosure, the human pharmacokinetic test under a pre-prandial (i.e., fasting) or a post-prandial condition (fed) through clinical trials was performed below, and meanwhile the incidence of adverse effects was investigated:

Experimental Sample:
i. The tizanidine hydrochloride liquid preparation prepared in Example 1:

| Material name | Role in formula | Unit measurement (g/1000 mL) |
|---|---|---|
| Tizanidine hydrochloride | Active ingredient | 0.46 |
| Sodium methyl paraben | Preservative | 1.00 |
| Sodium propyl paraben | Preservative | 0.10 |
| Disodium EDTA | Chelating agent | 1.00 |
| Sucralose | Sweetening agent | 0.50 |
| Citric acid | pH adjusting agent | 0.83 |
| Sodium citrate | pH adjusting agent | 0.42 |
| Strawberry flavoring agent | Flavoring agent | 0.50 |
| Purified water (appropriate amount) | Diluent | Making up to 1000 mL | ii. The tizanidine hydrochloride liquid preparation prepared in Example 2:

| Material name | Role in formula | Unit measurement (g/1000 mL) |
|---|---|---|
| Tizanidine hydrochloride | Active ingredient | 0.46 |
| Sodium methyl paraben | Preservative | 1.00 |
| Sodium propyl paraben | Preservative | 0.10 |
| 70% sorbitol | Co-solvent | 250.00 |
| Disodium EDTA | Chelating agent | 1.00 |
| Sucralose | Sweetening agent | 0.50 |
| Citric acid | pH adjusting agent | 0.90 |
| Sodium citrate | pH adjusting agent | 0.35 |
| Strawberry flavoring agent | flavoring agent | 0.50 |
| Purified water (appropriate amount) | Diluent | Making up to 1000 mL | iii. Zanaflex® (tizanidine hydrochloride) 4 mg tablet (standard 1);

iv. Zanaflex® (tizanidine hydrochloride) 4 mg capsule (standard 2).

Pre-Prandial (Fasting) Bioequivalence Test Method and Test Results:

This test was conducted in 25 healthy adult subjects under a pre-prandial condition, using a randomized, open-label, crossover, single-dose (4 mg as calculated in tizanidine), 5-cycle and 5-sequence crossover test design. The cycle washout period was 2 days. The subjects were fasted for at least 10 hours before administration, prohibited from drinking water one hour before and one hour after administration (except for 240 mL of water during administration), and provided with standard meals 4 hours and 8 hours after administration. The subjects were not allowed to eat food or beverages containing caffeine and/or xanthine (e.g., coffee, tea, soda water containing caffeine, cola, etc.), and were prohibited from eating grapefruit and/or grapefruit juice, and food containing poppy during the first 48 hours of each cycle and throughout the test period.

Administration Method:

The administration method of the liquid preparation was as follows: the subject maintained a sitting position, and 10 mL of i/ii was injected into the subject's mouth with an oral syringe, which was swallowed together with 50 mL of water by the subject. The syringe was rinsed by 10 mL of water, and the washing water was injected into the subject's mouth, which was repeated three times. Then the subject was provided with water to ensure that the total amount of water provided to the subject during the medicine taking was 240 mL. The subject kept a sitting position within two hours after taking the medicine.

The administration method of tablets/capsules was as follows: the subject maintained a sitting position, a single dose of iii/iv was placed in the subject's mouth, and swallowed in entirety with 240 mL of water (the subject was not allowed to chew or crush the tablets/capsules). The subject kept a sitting position within two hours after taking the medicine.

2.5 mL of blood samples of subjects in each cycle were collected before administration (0.00 h) and 0.08 h, 0.16 h, 0.25 h, 0.33 h, 0.50 h, 0.67 h, 0.83 h, 1.00 h, 1.25 h, 1.50 h, 1.75 h, 2.00 h, 2.50 h, 3.00 h, 4.00 h, 6.00 h, 8.00 h, 10.00 h and 12.00 h after administration, respectively. The relevant pharmacokinetic parameters were calculated.

$T_{max}$ is the peak time of the drug.

$C_{max}$ is the peak concentration, i.e., the maximum blood concentration measured.

$AUC_{0-t}$ was calculated by the linear trapezoidal method.

$AUC_{0-\infty} = AUC_{0-t} + Ct/\lambda z$. t is the sample collecting time of the last measurable blood drug concentration; Ct is the drug concentration of the last measurable sample, and $\lambda z$ is the terminal elimination rate constant.

TABLE 16

Results of human pharmacokinetic test under a pre-prandial condition

| Parameter(mean value) | i | ii | iii | iv |
|---|---|---|---|---|
| $C_{max}$ (pg/mL) | 6891.0570 | 6700.6869 | 6214.9907 | 6884.0184 |
| $AUC_{0-t}$ (pg·hr/mL) | 16452.1907 | 16750.9623 | 15326.0384 | 15937.0213 |
| $AUC_{0-\infty}$ (pg·hr/mL) | 16770.7496 | 17017.0368 | 15570.9400 | 16190.1320 |
| $T_{max}$ (hr) | 0.80 | 0.71 | 0.87 | 0.87 |

TABLE 17

Results of bioequivalence evaluation of i and iii under a pre-prandial condition

| Parameter | Lower 90% CI | Upper 90% CI | 90% CI Expandable Bioequivalent range | Result |
|---|---|---|---|---|
| $C_{max}$ | 84.51% | 125.59% | 69.56-143.76% | Equivalent |
| $AUC_{0-t}$ | 84.98% | 118.93% | 73.50-136.06% | Equivalent |
| $AUC_{0-\infty}$ | 85.75% | 117.62% | 74.87-133.57% | Equivalent |

TABLE 18

Results of bioequivalence evaluation of i and iv under a pre-prandial condition

| Parameter | Lower 90% CI | Upper 90% CI | 90% CI Expandable Bioequivalent range | Result |
|---|---|---|---|---|
| $C_{max}$ | 86.83% | 128.34% | 69.56-143.76% | Equivalent |
| $AUC_{0-t}$ | 92.29% | 128.55% | 73.50-136.06% | Equivalent |
| $AUC_{0-\infty}$ | 91.72% | 125.24% | 74.87-133.57% | Equivalent |

TABLE 19

Results of bioequivalence evaluation of ii and iii under a pre-prandial condition

| Parameter | Lower 90% CI | Upper 90% CI | 90% CI Expandable Bioequivalent range | Result |
|---|---|---|---|---|
| $C_{max}$ | 86.42% | 128.38% | 69.56-143.76% | Equivalent |
| $AUC_{0-t}$ | 87.94% | 123.02% | 73.50-136.06% | Equivalent |
| $AUC_{0-\infty}$ | 89.03% | 122.07% | 74.87-133.57% | Equivalent |

TABLE 20

Results of bioequivalence evaluation of ii and iv under a pre-prandial condition

| Parameter | Lower 90% CI | Upper 90% CI | 90% CI Expandable Bioequivalent range | Result |
|---|---|---|---|---|
| $C_{max}$ | 88.78% | 131.22% | 69.56-143.76% | Equivalent |
| $AUC_{0-t}$ | 95.47% | 132.99% | 73.50-136.06% | Equivalent |
| $AUC_{0-\infty}$ | 95.20% | 130.00% | 74.87-133.57% | Equivalent |

Conclusion: The tizanidine liquid preparation prepared by the present disclosure can achieve bioequivalence with the existing commercial standard product-Zanaflex® (tizanidine hydrochloride) 4 mg tablet/capsule under a pre-prandial condition.

Investigation Test and Test Results of Pre-Prandial (Fasting) Adverse Effects:

During the pre-prandial bioequivalence test, the adverse effects of the subjects during the whole experiment were recorded by means of observation, interview and active reporting.

TABLE 21

Investigation results of adverse effects and the incidence thereof under a pre-prandial condition

| Sample | i | ii | iii | iv |
|---|---|---|---|---|
| Drowsiness | None | 8% | 40% | 16% |
| Headache | None | None | None | None |
| Asthenia | None | None | None | None |
| Vertigo | None | 4.00% | None | None |
| Incidence of adverse effects | 0 | 12% | 40% | 16% |

As can be seen from the experimental results in the above table, the incidence of pre-prandial adverse effects (drowsiness, headache, asthenia, vertigo) in Example 1/Example 2 of the present disclosure was 0/12%, while the incidence of the adverse effects (drowsiness, headache, asthenia, vertigo) of tablets/capsules was 40%/16%. It can be seen that under a pre-prandial condition, the incidence of adverse effects (drowsiness, headache, asthenia, vertigo) of the tizanidine liquid preparation of the present disclosure was smaller than that of the existing solid preparations.

Post-Prandial Bioequivalence Test Method and Test Results:

The test was conducted in 27 healthy adult subjects under a post-prandial condition using a randomized, open-label, crossover, single-dose (tizanidine 4 mg), 8-cycle and 3-sequence partially replicated test design. The cycle washout period was 2 days. The subjects were fasted for at least 10 hours before administration, prohibited from drinking water one hour before and one hour after administration (except for 240 mL of water during administration), then provided with a high-calorie, high-fat, non-vegetable standard meal at 0.5 h before administration, administered within 0.5 h after the meal, and provided with a high-calorie, high-fat, non-vegetable standard meal at 4, 8, and 12 h after administration. The subjects were not allowed to eat food or beverages containing caffeine and/or xanthine (e.g., coffee, tea, soda water containing caffeine, cola, etc.), and were prohibited from eating grapefruit and/or grapefruit juice, and food containing poppy during the first 48 hours of each cycle and throughout the test period.

Administration Method:

The administration method of the liquid preparation was as follows: the subject maintained a sitting position, and 10 mL of i/ii was injected into the subject's mouth with an oral syringe, which was swallowed together with 50 mL of water by the subject. The syringe was rinsed by 10 mL of water, and the washing water was injected into the subject's mouth, which was repeated three times. Then the subject was provided with water to ensure that the total amount of water provided to the subject during the medicine taking was 240 mL. The subject kept a sitting position within two hours after taking the medicine.

The administration method of tablets/capsules was as follows: the subject maintained a sitting position, a single dose of iii/iv was placed in the subject's mouth, and swallowed in entirety with 240 mL of water (the subject was not allowed to chew or crush the tablets/capsules). The subject kept a sitting position within two hours after taking the medicine.

2.5 mL of blood samples of subjects in each cycle were collected before administration (0.00 h) and 0.08 h, 0.16 h, 0.25 h, 0.33 h, 0.50 h, 0.67 h, 0.83 h, 1.00 h, 1.25 h, 1.50 h, 1.75 h, 2.00 h, 2.50 h, 3.00 h, 4.00 h, 6.00 h, 8.00 h, 10.00 h and 12.00 h after administration, respectively. The relevant pharmacokinetic parameters were calculated.

$C_{max}$ is the peak concentration, i.e., the maximum blood concentration measured.

$AUC_{0-t}$ was calculated by the linear trapezoidal method.

$AUC_{0-\infty} = AUC_{0-t} + Ct/\lambda z$. t is the sample collecting time of the last measurable blood drug concentration; Ct is the drug concentration of the last measurable sample, and $\lambda z$ is the terminal elimination rate constant.

TABLE 22

Results of human pharmacokinetic test under a post-prandial condition

| Parameter(mean value) | i | ii | iii | iv |
|---|---|---|---|---|
| $C_{max}$ (pg/mL) | 4879.123 | 4852.799 | 5395.440 | 4832.833 |
| $AUC_{0-t}$ (pg · hr/mL) | 14551.615 | 14810.490 | 14943.559 | 15267.928 |
| $AUC_{0-\infty}$ (pg · hr/mL) | 14783.945 | 15051.702 | 15180.678 | 15557.618 |
| $T_{max}$ (hr) | 0.94 | 1.00 | 1.74 | 2.02 |

In the above table, the $T_{max}$ of the tizanidine hydrochloride liquid preparation of Example 1/Example 2 of the present disclosure was 0.94/1.00 hour; whereas the $T_{max}$ of the existing (tizanidine hydrochloride) tablet/capsule was 1.74/2.02 hour. It can be seen that under the post-prandial condition, the $T_{max}$ of the liquid preparation of the present disclosure was significantly lower than that of the existing solid preparation, indicating that the drug action was obviously accelerated.

According to the comparison results of Table 16 and Table 22, it can be seen that the $T_{max}$ of the tizanidine hydrochloride liquid preparation of Example 1/Example 2 of the present disclosure under the post-prandial condition was only 0.14/0.29 hours longer than that under the pre-prandial condition, while the $T_{max}$ of the existing tablet/capsule under the post-prandial condition was 0.87/1.15 hours longer than that under the pre-prandial condition. It can be seen that the impact of food on the $T_{max}$ of the present disclosure is less than its impact on the existing solid preparations.

It can be seen that the effect of food on the drug action speed of the tizanidine hydrochloride liquid preparation of the present disclosure is less than its effect on the existing solid preparation; under the post-prandial condition, the present disclosure has a faster drug action than the existing solid preparations.

Since the post-prandial bioequivalence test method used a partially replicated test design, it is well known to those skilled in the art that if the $S_{WR}$ (intra-individual standard deviation)≥0.294 (i.e., ISCV %≥30%), the RSABE method can be used for equivalence evaluation (applying to any or all of $AUC_{0-t}$, $AUC_{0-\infty}$, $C_{max}$)—The standard for determining whether the pharmacokinetic parameters ($AUC_{0-t}$, $AUC_{0-\infty}$, or $C_{max}$) of the test preparation and reference preparation are bioequivalent by using RSABE method is: the point estimate of the geometric mean ratio of the calculated parameter (hereinafter referred to as the point estimate) is within the range of 80%-125%, and meanwhile, the upper limit of the one-sided 95% confidence interval of the calculated parameter (abbreviated as 95% confidence upper limit)≤50. If $S_{WR}$<0.294 (i.e., ISCV %<30%), the ABE method should be used to evaluate the bioequivalence.

TABLE 23-1

Results of $C_{max}$ bioequivalence evaluation of i and iii under a post-prandial condition

| Parameter | ISCV % | Point estimate (%) | 95% confidence upper limit | Result |
|---|---|---|---|---|
| $C_{max}$ | 51.62% | 98.60% | −0.1251 | Equivalent |

TABLE 23-2

Results of $AUC_{0-t}$ and $AUC_{0-\infty}$ bioequivalence evaluation of i and iii under a post-prandial condition

| Parameter | ISCV % | Lower 90% CI | Upper 90% CI | 90% CI equivalent range | Result |
|---|---|---|---|---|---|
| $AUC_{0-t}$ | 25.75% | 94.27% | 115.44% | 80.00-125.00% | Equivalent |
| $AUC_{0-\infty}$ | 25.62% | 94.48% | 115.54% | 80.00-125.00% | Equivalent |

TABLE 24-1

Results of $C_{max}$ bioequivalence evaluation of i and iv under a post-prandial condition

| Parameter | ISCV % | Point estimate (%) | 95% confidence upper limit | Result |
|---|---|---|---|---|
| $C_{max}$ | 33.64% | 108.39% | −0.0241 | Equivalent |

TABLE 24-2

Results of $AUC_{0-t}$ and $AUC_{0-\infty}$ bioequivalence evaluation of i and iv under a post-prandial condition

| Parameter | ISCV % | Lower 90% CI | Upper 90% CI | 90% CI equivalent range | Result |
|---|---|---|---|---|---|
| $AUC_{0-t}$ | 26.04% | 92.62% | 116.22% | 80.00-125.00% | Equivalent |
| $AUC_{0-\infty}$ | 25.46% | 92.50% | 115.82% | 80.00-125.00% | Equivalent |

TABLE 25-1

Results of $C_{max}$ bioequivalence evaluation of ii and iii under a post-prandial condition

| Parameter | ISCV % | Point estimate (%) | 95% confidence upper limit | Result |
|---|---|---|---|---|
| $C_{max}$ | 51.62% | 103.73% | −0.122 | Equivalent |

TABLE 25-2

Results of $AUC_{0-t}$ and $AUC_{0-\infty}$ bioequivalence evaluation of ii and iii under a post-prandial condition

| Parameter | ISCV % | Lower 90% CI | Upper 90% CI | 90% CI equivalent range | Result |
|---|---|---|---|---|---|
| $AUC_{0-t}$ | 25.97% | 104.12% | 123.69% | 80.00-125.00% | Equivalent |
| $AUC_{0-\infty}$ | 25.74% | 104.30% | 123.74% | 80.00-125.00% | Equivalent |

TABLE 26-1

Results of $C_{max}$ bioequivalence evaluation of
ii and iv under a post-prandial condition

| Parameter | ISCV % | Point estimate (%) | 95% confidence upper limit | Result |
|---|---|---|---|---|
| $C_{max}$ | 33.64% | 114.46% | −0.0041 | Equivalent |

TABLE 26-2

Results of $AUC_{0-t}$ and $AUC_{0-\infty}$ bioequivalence
evaluation of ii and iv under a post-prandial condition

| Parameter | ISCV % | Lower 90% CI | Upper 90% CI | 90% CI equivalent range | Result |
|---|---|---|---|---|---|
| $AUC_{0-t}$ | 25.85% | 103.32% | 122.33% | 80.00-125.00% | Equivalent |
| $AUC_{0-\infty}$ | 25.30% | 103.10% | 121.88% | 80.00-125.00% | Equivalent |

Conclusion: The tizanidine liquid preparation prepared by the present disclosure can achieve bioequivalence with the existing commercial standard product-Zanaflex® (tizanidine hydrochloride) 4 mg tablet/capsule under a post-prandial condition.

Investigation Test and Test Results of Post-Prandial Adverse Effects:

During the post-prandial bioequivalence test, the adverse effects of the subjects during the whole experiment were recorded by means of observation, interview and active reporting.

TABLE 27

Investigation results of adverse effects and the
incidence thereof under a post-prandial condition

| Sample | i | ii | iii | iv |
|---|---|---|---|---|
| Drowsiness | 1.85% | 1.85% | 25.93% | 22.22% |
| Vomiting | None | None | None | 1.85% |
| Headache | None | None | 3.70% | 1.85% |
| Incidence of adverse effects | 1.85% | 1.85% | 29.63% | 25.92% |

As can be seen from the experimental results in the above table, the incidence of post-prandial adverse effects (drowsiness, vomiting, headache) in Example 1/Example 2 of the present disclosure was 1.85%/1.85%, whereas the incidence of the adverse effects (drowsiness, vomiting, headache) of tablets/capsules was 29.63%/25.92%. It can be seen that under a post-prandial condition, the incidence of adverse effects (drowsiness, vomiting, headache) of the tizanidine liquid preparation of the present disclosure was smaller than that of the existing solid preparations.

From the investigation results of the adverse effects and the incidence thereof in Table 21 and Table 27, it can be seen that the incidence of the adverse effect—drowsiness of the tizanidine liquid preparation of the present disclosure under the pre-prandial/post-prandial conditions was both smaller than that of the solid preparations (i.e. tablet and capsule preparations); the incidence of the adverse effect item—headache under the post-prandial condition was smaller than that of the solid preparations (i.e. tablet and capsule preparations); and the incidence of the adverse effect—vomiting under the post-prandial condition was smaller than that of the capsule preparation.

It can be seen that the incidence of adverse effects of the tizanidine liquid preparation of the present disclosure is smaller than that of the existing solid preparations, no matter under the pre-prandial or post-prandial conditions. The liquid preparation of the present disclosure changes the pharmaceutical dosage form of tizanidine and the related excipients, thereby significantly reducing the drug adverse reactions, which is unexpected by those skilled in the art. The reduction of the adverse effects rate of the medicine of the present disclosure improves the safety of the drug use and the compliance of patients taking the medicine in the present disclosure.

To sum up, the tizanidine liquid preparation of the present disclosure has low impurity content and strong stability. Compared with the existing tizanidine solid preparations, the tizanidine liquid preparation has low adverse effects rate, little effect of food on the drug action speed, fast drug action speed under a post-prandial condition, and equivalent bioavailability to the existing solid preparations, which satisfies the clinical needs.

Example 7

A larger study involving 115 subjects was conducted. All methods and materials are the same as those used in Example 6. Test (T) refers to the composition of the present disclosure, while Reference (R) refers to the tablet form of Zanaflex®.

TABLE 28

Summary Statistics of Pharmacokinetics Data between Test (T) and Reference
(R) Products for Tizanidine under Fasting Condition (N = 115)

| Treatment | $C_{max}$ (pg/mL) Mean (Min-Max) | $AUC_{0-t}$ (hr*pg/mL) Mean (Min-Max) | $AUC_{0-\infty}$ (hr*pg/mL) Mean (Min-Max) | $T_{max}$ (hr) Median (Min-Max) | $t_{1/2}$ (hr) Mean (Min-Max) |
|---|---|---|---|---|---|
| Test (T) | 6238 (402-19485) | 18256 (984-49489) | 18657 (1442-51154) | 0.830 (0.33-2.33) | 1.620 (1.073-3.070) |
| Reference (R) | 5827 (477-17300) | 16470 (978-48096) | 16860 (1603-48967) | 1.00 (0.33-3.00) | 1.593 (0.959-3.053) |

TABLE 29

Results of Geometric Least Square Mean, Power (%), T/R Ratios, ISCV (%), 90% CI of Test (T) versus Reference (R) based on Ln-transformed Data for Tizanidine under Fasting Condition (N = 115)

| Parameters (Units) | Geometric Least Square mean | | Power (%) | Ratio (%) | ISCV (%) | 90% CI | Acceptance Criteria (%) | Outcome of BE result |
|---|---|---|---|---|---|---|---|---|
| | Test | Reference | | | | | | |
| $C_{max}$ (pg/mL) | 5069.2 | 4689.3 | 100.00 | 108.10 | 24.69 | 102.49 to 114.02 | 80.00-125.00 | Bioequivalent |
| $AUC_{0-t}$ (hr*pg/mL) | 14108.2 | 12751.5 | 100.00 | 110.64 | 19.06 | 106.15 to 115.31 | 80.00-125.00 | |
| $AUC_{0-\infty}$ (hr*pg/mL) | 14690.5 | 13319.5 | 100.00 | 110.29 | 18.46 | 105.96 to 114.81 | 80.00-125.00 | |

For the $C_{max}$ value of 5069, the 80-125% range is 4055-6336. For the $C_{max}$ value of 4689, the 80-125% range is 3751-5861.

For the $AUC_{0-t}$ value of 14108, the 80-125% range is 11286-17635. For the $AUC_{0-t}$ value of 12751, the 80-125% range is 10200-15938.

For the $AUC_{0-\infty}$ value 14690, the 80-125% range is 11752 and 18362. For the $AUC_{0-\infty}$ value 13319, the 80-125% range is 10655 and 16648.

TABLE 30

Summary Statistics of Pharmacokinetics Data between Test (T) and Reference (R) Products for Tizanidine under Fed Condition (N = 115)

| Treatment | $C_{max}$ (pg/mL) Mean (Min-Max) | $AUC_{0-t}$ (hr*pg/mL) Mean (Min-Max) | $AUC_{0-\infty}$ (hr*pg/mL) Mean (Min-Max) | $T_{max}$ (hr) Median (Min-Max) | $t_{1/2}$ (hr) Mean (Min-Max) |
|---|---|---|---|---|---|
| Test (T) | 6321 (845-14301) | 22816 (2516-71274) | 23463 (2780-73520) | 0.830 (0.250-4.00) | 1.747 (1.010-3.002) |
| Reference (R) | 6146 (476-18181) | 21019 (1676-63192) | 21537 (2045-64982) | 1.500 (0.33-6.00) | 1.676 (0.915-2.754) |

TABLE 31

Results of Geometric Least Square Mean, Power (%), T/R Ratios, ISCV (%), 90% CI of Test (T) versus Reference (R) based on Ln-transformed Data for Tizanidine under fed Condition (N = 115)

| Parameters (Units) | Geometric Least Square mean | | Power (%) | Ratio (%) | ISCV (%) | 90% CI | Acceptance Criteria (%) | Outcome of BE result |
|---|---|---|---|---|---|---|---|---|
| | Test | Reference | | | | | | |
| $C_{max}$ (pg/mL) | 5473.3 | 5116.8 | 99.99 | 106.97 | 28.58 | 100.60 to 113.74 | 80.00-125.00 | Bioequivalent |
| $AUC_{0-t}$ (hr*pg/mL) | 19256.7 | 17479.5 | 100.00 | 110.17 | 11.47 | 107.44 to 112.96 | 80.00-125.00 | |
| $AUC_{0-\infty}$ (hr*pg/mL) | 19759.6 | 17974.5 | 100.00 | 109.93 | 11.22 | 107.26 to 112.67 | 80.00-125.00 | |

For the $C_{max}$ value of 5473, the 80-125% range is 4378-6841. For the $C_{max}$ value of 5116, the 80-125% range is 4092-6395.

For the AUC0-t value of 19256, the 80-125% range is 15404-24070. For the AUC0-t value of 17479, the 80-125% range is 13983-21848.

For the AUC0-∞ value 19759, the 80-125% range is 15807 and 24698. For the $AUC_{0-\infty}$ value 17974, the 80-125% range is 14379 and 22467.

Example 8

Another study involving 62 subjects was conducted to compare the pharmacokinetics of the disclosed liquid composition with Zanaflex® capsules under fed condition. All methods and materials are the same as those used in Example 6. Test (T) refers to the composition of the present disclosure, while Reference (R) refers to the capsule form of Zanaflex®.

TABLE 32

Summary Statistics of Pharmacokinetics Data between Test (T) Vs Reference (R) Products for Tizanidine under Fed Condition (N = 62)

| Treatment | Cmax (pg/mL) Mean (Min-Max) | AUC0-t (hr*pg/mL) Mean (Min-Max) | AUC0-∞ (hr*pg/mL) Mean (Min-Max) | Tmax (hr) Median (Min-Max) | t½ (hr) Mean (Min-Max) |
|---|---|---|---|---|---|
| Test (T) | 5319 (1676-13544) | 18548 (5140-56476) | 18986 (5443-58028) | 0.67 (0.33-3.00) | 1.673 (1.166-2.241) |
| Reference (R) | 6263 (852-30397) | 17190 (2403-60615) | 18044 (2980-65066) | 1.25 (0.33-4.00) | 1.574 (1.001-2.735) |

TABLE 33

Results of Geometric Least Square Mean, Power (%), T/R Ratios, ISCV (%), 90% CI of Test (T) versus Reference (R) based on Ln-transformed Data for Tizanidine under Fed Condition (N = 62)

| Parameters (Units) | Geometric Least Square mean Test | Geometric Least Square mean Reference | Power (%) | Ratio (%) | ISCV (%) | 90% CI | Acceptance Criteria (%) | Outcome of BE result |
|---|---|---|---|---|---|---|---|---|
| Cmax (pg/mL) | 4805 | 5136 | 92.22 | 93.55 | 36.63 | 84.02 to 104.17 | 80.00-125.00 | Bioequivalent |
| AUC0-t (hr*pg/mL) | 16238 | 14346 | 99.17 | 113.19 | 27.16 | 104.40 to 122.72 | 80.00-125.00 | |
| AUC0-∞ (hr*pg/mL) | 16684 | 14950 | 99.28 | 111.59 | 26.40 | 103.04 to 120.85 | 80.00-125.00 | |

The above description of the disclosed embodiments enables those skilled in the art to realize or use the present disclosure. Various modifications to these embodiments will be readily obvious to those skilled in the art, and the generic principles defined herein may be realized in other embodiments without departing from the spirit or scope of the present disclosure. Thus, the present disclosure is not intended to be limited to the embodiments shown herein, but is to be accorded the widest scope consistent with the principles and novel features disclosed herein.

The invention claimed is:

1. A liquid pharmaceutical composition, comprising
 a) about 0.1-2 mg/mL of tizanidine hydrochloride;
 b) about 0.5-5 mM of EDTA;
 c) water,
 d) about 2-6 mM citric acid,
 e) about 0.5-3 mM sodium citrate, and
 a pharmaceutically acceptable excipient,
 wherein pH of the liquid pharmaceutical composition is between 3.5 and 6.1, and
 wherein the liquid pharmaceutical composition retains at least 99% tizanidine concentration as measured by USP assay when stored at room temperature for at least 30 days.

2. The pharmaceutical composition of claim 1, further comprising
 f) about 2-10 mM of sodium methylparaben; and
 g) about 0.2-1 mM of sodium propylparaben.

3. The pharmaceutical composition of claim 2, further comprising
 h) about 0.5-5 mM of sucralose.

4. The pharmaceutical composition of claim 1, wherein the EDTA is disodium EDTA.

5. The pharmaceutical composition of claim 1, wherein the liquid pharmaceutical composition retains at least 99% tizanidine concentration as measured by USP assay when stored at room temperature for at least 180 days.

6. The pharmaceutical composition of claim 1, wherein the liquid pharmaceutical composition has a formula selected from the group consisting of Formula I-Formula V:
 Formula I: tizanidine hydrochloride 0.46 mg/ml, hydroxypropyl cellulose 0.025 g/mL, colloidal silicon dioxide 5 mg/mL, 70% sorbitol solution 0.15 g/mL, sodium methylparaben 1 mg/mL, sodium propylparaben 0.1 mg/mL, disodium EDTA 1 mg/mL, sucralose 0.5 mg/mL, citric acid 0.90 mg/mL, sodium citrate 0.46 mg/mL, with remainder being water and optionally flavoring agent;
 Formula II: tizanidine hydrochloride 0.46 mg/mL, 70% sorbitol solution 0.25 g/mL, sodium methylparaben 1 mg/mL, sodium propylparaben 0.1 mg/mL, disodium EDTA 1 mg/mL, sucralose 0.5 mg/mL, citric acid 0.90 mg/mL, sodium citrate 0.35 mg/mL, with remainder being water and optionally flavoring agent;
 Formula III: tizanidine hydrochloride 0.46 mg/mL, hydroxypropyl cellulose 0.025 g/mL, 70% sorbitol solution 0.15 g/mL, sodium methylparaben 1 mg/mL, sodium propylparaben 0.1 mg/mL, disodium EDTA 1 mg/mL, sucralose 0.5 mg/mL, citric acid 0.90 mg/mL, sodium citrate 0.46 mg/mL, with remainder being water and optionally flavoring agent;
 Formula IV: tizanidine hydrochloride 0.46 mg/mL, sodium methylparaben 1 mg/mL, sodium propylparaben 0.1 mg/mL, disodium EDTA 1 mg/mL, sucralose 0.5 mg/mL, citric acid 0.83 mg/mL, sodium citrate 0.42 mg/mL, with remainder being water and optionally flavoring agent; and
 Formula V: tizanidine hydrochloride 0.46 mg/mL, hydroxypropyl cellulose 0.05 g/mL, sodium benzoate 1 mg/mL, glycerin 0.15 g/mL, 70% sorbitol solution 0.25 g/mL, disodium EDTA 1 mg/mL, sucralose 0.5 mg/mL, with remainder being water and optionally flavoring agent.

7. A liquid pharmaceutical composition for treating muscle spasm in a subject, comprising
   a) about 0.1-2 mg/mL of tizanidine hydrochloride;
   b) about 0.5-5 mM of EDTA; and
   c) water, and
   a pharmaceutically acceptable excipient,
   wherein pH of the pharmaceutical composition is between 3.5 and 6.1, and wherein the liquid pharmaceutical composition retains at least 99% tizanidine concentration as measured by USP assay for at least 30 days when stored at room temperature, wherein said liquid pharmaceutical composition causes lower incidence rate of adverse effect in the subject as compared to incidence rate of adverse effect caused by solid tablets or capsules of tizanidine at the same dosage.

8. The pharmaceutical composition of claim 7, wherein the adverse effect comprises at least one of: headache, dizziness, sedation, vomiting, nausea drowsiness, asthenia, vertigo, or combination thereof.

9. The liquid pharmaceutical composition of claim 7, wherein the liquid pharmaceutical composition causes less drowsiness when administered to patients with muscle spasm as compared to drowsiness caused by solid tablets or capsules of tizanidine at the same dosage.

10. The liquid pharmaceutical composition of claim 7, wherein the liquid pharmaceutical composition causes lower incidence rate of drowsiness when administered to patients with muscle spasm as compared to incidence rate of drowsiness caused by solid tablets or capsules of tizanidine at the same dosage.

11. The pharmaceutical composition of claim 7, further comprising
   d) about 2-6 mM citric acid, and
   e) about 0.5-3 mM sodium citrate.

12. The pharmaceutical composition of claim 11, further comprising
   f) about 2-10 mM of sodium methylparaben; and
   g) about 0.2-1 mM of sodium propylparaben.

13. The pharmaceutical composition of claim 12, further comprising
   h) about 0.5-5 mM of sucralose.

14. The pharmaceutical composition of claim 13, wherein the pharmaceutical composition further comprises a flavoring agent.

15. The pharmaceutical composition of claim 3, wherein the strawberry aromatic agent is present in the pharmaceutical composition at about 0.5 mg/mL.

16. A method of administering tizanidine to a subject in need thereof for muscle relaxation, comprising administering a liquid pharmaceutical composition orally to said subject, wherein the pharmaceutical composition comprises
   a) about 0.1-2 mg/mL of tizanidine hydrochloride;
   b) about 0.5-5 mM of EDTA; and
   c) water,
   wherein pH of the liquid pharmaceutical composition is between 3.5 and 6.1, and
   wherein the liquid pharmaceutical composition retains at least 99% tizanidine concentration as measured by USP assay when stored at room temperature for at least 30 days.

17. The method of claim 16, wherein the liquid pharmaceutical composition of claim 1 is administered to the subject either before meal or after meal with same clinical effect.

18. The method of claim 16, wherein said liquid pharmaceutical composition causes less or fewer adverse effects in the subject as compared to side effects caused by solid tablets or capsules of tizanidine at the same dosage.

19. The method of claim 16, wherein the pharmaceutical composition further comprises
   d) about 2-6 mM citric acid, and
   e) about 0.5-3 mM sodium citrate.

20. The method of claim 19, wherein the pharmaceutical composition further comprises
   f) about 2-10 mM of sodium methylparaben; and
   g) about 0.2-1 mM of sodium propylparaben.

21. The method of claim 20, wherein the pharmaceutical composition further comprises
   h) about 0.5-5 mM of sucralose.

22. The method of claim 18, wherein the adverse effect comprises at least one of headache, dizziness, sedation, nausea drowsiness, asthenia, vertigo, or combination thereof.

23. The method of claim 22, wherein the liquid pharmaceutical composition causes lower incidence rate of drowsiness when administered to the subject as compared to incidence rate of drowsiness caused by solid tablets or capsules of tizanidine at the same dosage.

24. The pharmaceutical composition of claim 1, wherein when a single dose of the liquid pharmaceutical composition is administered to a subject, the mean value of $C_{max}$, $AUC_{0-t}$, or $AUC_{0-\infty}$ is within 80% to 125% of the mean value of $C_{max}$, $AUC_{0-t}$, or $AUC_{0-\infty}$, respectively, of the same amount of tizanidine in a solid dosage form.

25. The pharmaceutical composition of claim 1, wherein when a single dose of the pharmaceutical composition is administered to a subject under fasting condition, mean value of $C_{max}$ is between 4055 and 6336 pg/mL, or between 3751 and 5861 pg/mL, or mean value of $AUC_{0-t}$ is between 11286 and 17635 hr*pg/mL, or between 10200 and 15938 hr*pg/mL, or mean value of $AUC_{0-\infty}$ is between 11752 and 18362 hr*pg/mL or between 10655 and 16648 hr*pg/mL.

26. The pharmaceutical composition of claim 1, wherein when a single dose of the pharmaceutical composition is administered to a subject under fed condition, mean value of $C_{max}$ is between 4378 and 6841 pg/mL, or between 4092 and 6395 pg/mL, or mean value of $AUC_{0-t}$ is between 15404 and 24070 hr*pg/mL, or between 13983 and 21848 hr*pg/mL, or mean value of $AUC_{0-\infty}$ is between 15807 and 24698 hr*pg/mL or between 14379 and 22467 hr*pg/mL.

27. The pharmaceutical composition of claim 7, wherein when a single dose of the liquid pharmaceutical composition is administered to a subject, the mean value of $C_{max}$, $AUC_{0-t}$, or $AUC_{0-\infty}$ is within 80% to 125% of the mean value of $C_{max}$, $AUC_{0-t}$, or $AUC_{0-\infty}$, respectively, of the same amount of tizanidine in a solid dosage form.

28. The pharmaceutical composition of claim 7, wherein when a single dose of the pharmaceutical composition is administered to a subject under fasting condition, mean value of $C_{max}$ is between 4055 and 6336 pg/mL, or between 3751 and 5861 pg/mL, or mean value of $AUC_{0-t}$ is between 11286 and 17635 hr*pg/mL, or between 10200 and 15938 hr*pg/mL, or mean value of $AUC_{0-\infty}$ is between 11752 and 18362 hr*pg/mL or between 10655 and 16648 hr*pg/mL.

29. The pharmaceutical composition of claim 7, wherein when a single dose of the pharmaceutical composition is administered to a subject under fed condition, mean value of $C_{max}$ is between 4378 and 6841 pg/mL, or between 4092 and 6395 pg/mL, or mean value of $AUC_{0-t}$ is between 15404 and 24070 hr*pg/mL, or between 13983 and 21848 hr*pg/mL, or mean value of $AUC_{0-\infty}$ is between 15807 and 24698 hr*pg/mL or between 14379 and 22467 hr*pg/mL.

* * * * *